US009050371B2

(12) United States Patent
Beals et al.

(10) Patent No.: US 9,050,371 B2
(45) Date of Patent: Jun. 9, 2015

(54) PEGYLATED INSULIN LISPRO COMPOUNDS

(75) Inventors: John Michael Beals, Indianapolis, IN (US); Gordon Butler Cutler, Jr., Deltaville, VA (US); Ryan John Hansen, Riverton, UT (US); Shun Li, Carmel, IN (US); Lianshan Zhang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/481,111

(22) Filed: Jun. 9, 2009

(65) Prior Publication Data

US 2009/0312236 A1 Dec. 17, 2009

Related U.S. Application Data

(60) Provisional application No. 61/061,281, filed on Jun. 13, 2008, provisional application No. 61/121,394, filed on Dec. 10, 2008.

(51) Int. Cl.
*C07K 14/62* (2006.01)
*A61K 38/28* (2006.01)
*A61K 47/48* (2006.01)

(52) U.S. Cl.
CPC ........... *A61K 47/48215* (2013.01); *A61K 38/28* (2013.01)

(58) Field of Classification Search
None
See application file for complete search history.

(56) References Cited

U.S. PATENT DOCUMENTS

| 4,179,337 | A | 12/1979 | Davis et al. |
| 6,034,054 | A | 3/2000 | DeFelippis |
| 6,174,856 | B1 | 1/2001 | Langballe et al. |
| 6,551,992 | B1 | 4/2003 | DeFelippis |
| 6,734,162 | B2 * | 5/2004 | Van Antwerp et al. ........... 514/2 |
| 6,890,518 | B2 * | 5/2005 | Patton et al. .................... 424/45 |
| 6,906,028 | B2 | 6/2005 | DeFelippis |
| 2006/0171920 | A1 | 8/2006 | Shechter et al. |
| 2007/0083006 | A1 | 4/2007 | Hinds et al. |
| 2008/0171848 | A1 | 7/2008 | Christiansen et al. |
| 2009/0304665 | A1 * | 12/2009 | Frost et al. ................... 424/94.5 |
| 2009/0306337 | A1 * | 12/2009 | Madsen et al. ................ 530/303 |

FOREIGN PATENT DOCUMENTS

| EP | 1 172 114 A | 1/2002 |
| EP | 1 845 105 A | 10/2007 |
| WO | WO 02/065985 A2 | 8/2002 |
| WO | WO 02/098446 A1 | 12/2002 |
| WO | WO 2004/091494 | 10/2004 |
| WO | WO 2006/079641 | 8/2006 |
| WO | WO 2006/097521 A | 9/2006 |
| WO | WO 2006/124529 A | 11/2006 |
| WO | WO 2007/075534 A | 7/2007 |
| WO | WO 2008/015099 | 2/2008 |
| WO | WO 2008/084051 | 7/2008 |

OTHER PUBLICATIONS

Holleman et al. 1997. New England J. Med. 337:176-183.*
rxlist.com/humalog-drug, updated Aug. 6, 2007, downloaded Apr. 8, 2010.*
www.druginfo.com/pharmacopeia, 2005, downloaded Apr. 8, 2010.*
www.clinicalreview.com, modified 2008, downloaded Apr. 9, 2010.*
Greenwald, "PEG drugs: an overview", Journal of Controlled Release, 2001, pp. 159-171, vol. 74, No. 1-3.
Greenwald, "Effective drug delivery by PEGylated drug conjugates", Advanced Drug Delivery Reviews, 2003, pp. 217-250, vol. 55, No. 2.
Dunn, "Zinc-Ligand Interactions Modulate Assembly and Stability of the Insulin Hexamer—A Review," *BioMetals*, vol. 18, pp. 295-303 (2005).
Dou "Synthesis and Purification of Mono-PEGylated Insulin," *Chem Biol Drug Des*, vol. 69, pp. 132-138(2007).
Hinds, "Effects of PEG Conjugation on Insulin Properties," *Advanced Drug Delivery Reviews*, vol. 54, pp. 505-530 (2002).
Hinds, "Synthesis and Characterization of Poly(ethylene glycol)-Insulin Conjugates," *Bioconjugate Chem.*, vol. 11, pp. 195-201 (2000).
Schmidt, "PEGylated Bioactive Molecules In Biodegradable Polymer Microparticles," *Expert Opinion Biol. Ther.*, vol. 7, pp. 1427-1436 (2007).
Abuchowski, "PEGylation: Changing the Landscape of Protein Drug Delivery, an Interview With Abe Abuchowski, Ph.D.," *Prolong Pharmaceuticals Teaching Away*, pp. 1-6 (2006).
Heise, "Lower Within-Subject Variability of Insulin Detemir in Comparison to NPH Insulin and Insulin Glargine in People With Type 1 Diabetes," American Diabetes Association, 2004, pp. 1614-1620, vol. 53.
Document from WIPO Examination of related application: "Demand" and "Reply to Written Opinion and Amendments Under Article 34", Apr. 9, 2010.
Document from WIPO Examination of related application: "Notification Concerning Informal Communications With the Applicant", Jul. 13, 2010.
Document from WIPO Examination of related application: "Reply to Notification Concerning Informal Communications With the Applicant and Amendments Under Article 34", Aug. 12, 2010.
Document from WIPO Examination of related application: "International Preliminary Report on Patentability", Sep. 3, 2010.
Document from WIPO Examination of related application: "Written Opinion of the International Search Authority," Oct. 12, 2009, available at https://register.epo.org/espacenet/application?number=EP09763419&lng=en&tab=doclist.

(Continued)

*Primary Examiner* — Michael Pak
(74) *Attorney, Agent, or Firm* — Duane C. Marks; Nelsen L. Lentz

(57) ABSTRACT

The present invention relates to the field of diabetes. More particularly, the invention relates to PEGylated insulin lispro compounds that are PEGylated with high molecular weight poly(ethylene glycol), are highly soluble at physiological pH, have an extended duration of action, and characterized by pharmacokinetic, pharmacodynamic, and/or activity peak-trough ratios of less than 2. The invention also relates to methods of providing such molecules, to pharmaceutical compositions containing them, and to their therapeutic uses.

4 Claims, 2 Drawing Sheets

(56) References Cited

OTHER PUBLICATIONS

Cliff Mintz, Biotech Pioneer, Life Science Leader, May 2009, pp. 8-13, available at www.parsec-corp.com/downloads/2009MayIssue_LifeScienceLeader.pdf.

Cambridge Healthtech Institute, PEGylation: Changing the Landscape of Protein Drug Delivery: An Interview with Abe Abuchowski, PhD, Cambridge Healthtech Institute Molecular Med Monthly, Issue 76, Mar. 2007.

Shojaee-Moradie et al., "Novel Hepatoselective Insulin Analog, Studies with a covalently linked thyroxyl-insulin complex in humans", Diabetes Care, vol. 23 No. 8, pp. 1124-1129 (2000).

Shojaee-Moradie, et al., "Demonstration of a relatively hepatoselective effect of covalent insulin dimers on glucose metabolism in dogs", Diabetologia, vol. 38, pp. 1007-1013 (1995).

Smeeton, et al., "Differential effects of insulin detemir and neutral protamine Hagedorn (NPH) insulin on hepatic glucose production and peripheral glucose uptake during hypoglycaemia in type 1 diabetes", Diabetologia, vol. 52, pp. 2317-2323 (2009).

Brems, et al., "Altering the association properties of insulin by amino acid replacement", Protein Engineering, vol. 5, No. 6, pp. 527-533 (1992).

Herring, et al., "Hepatoselectivity and the evolution of insulin", Diabetes Obesity and Metabolism, vol. 16, pp. 1-8 (2014).

Hordern, et al., "Comparison of the effects on glucose and lipid metabolism of equipotent doses of insulin detemir and NPH insulin with a 16-h euglycaemic clamp", Diabetologia, vol. 48, pp. 420-426 (2005).

European Medicines Agency, "CHMP Safety Working Party's response to the PDCO regarding the use of PEGylated drug products in the paediatric population", Nov. 16, 2012, EMA/CHMP/SWP/647258/2012.

Sinha, et al., "Single-Dose Pharmacokinetics and Glucodynamics of the Novel, Long-Acting Basal Insulin LY2605541 in Healthy Subjects", Journal of Clinical Pharmacology, vol. 54(7), pp. 792-799 (2014).

Henry, et al., "Basal Insulin Peglispro Demonstrates Preferential Hepatic Versus Peripheral Action Relative to Insulin Glargine in Healthy Subjects", Diabetes Care, vol. 37, pp. 2609-2615 (2014).

Bergenstal, et al., "Lower Glucose Variability and Hypoglycemia Measured by Continuous Glucose Monitoring with Novel Long-Acting Insulin LY2605541 Versus Insulin Glargine", Diabetes Care, vol. 37, pp. 659-665 (2014).

Jansen, et al., "Pronounced weight gain in insulin-treated patients with type 2 diabetes mellitus is associated with an unfavourable cardiometabolic risk profile", The Netherlands Journal of Medicine, vol. 68(11), pp. 359-366 (2010).

Lee and Aronne, "Weight Management for Type 2 Diabetes Mellitus: Global Cardiovascular Risk Reduction", American Journal of Cardiology, vol. 99(4A), pp. 68B-79B (2007).

Jacober, et al., "Contrasting weight changes with LY2605541, a novel long-acting insulin, and insulin glargine despite similar improved glycaemic control in T1DM and T2DM", Diabetes Obesity and Metabolism, vol. 16, pp. 351-356 (2014).

Rosenstock, et al., "Better Glycemic Control and Weight Loss With the Novel Long-Acting Basal Insulin LY2605541 Compared With Insulin Glargine in Type 1 Diabetes", Diabetes Care, vol. 36, pp. 522-528 (2013).

E.J. Bastyr, et al., "The Novel Long-Acting Insulin LY2605541 is Superior to Insulin Glargine in Lowering Intra-Day Glucose Variability and Hypoglycemia Event Rate from Continuous Glucose Monitoring (CGM) in Patients With Type 2 Diabetes", Diabetes 2012 61; A90: 346-OR.

E.J. Bastyr, et al., "The Novel Long-Acting Insulin LY2605541 is Superior to Insulin Glargine in Lowering Intra-Day Glucose Variability and Hypoglycemia Event Rate from Continuous Glucose Monitoring (CGM) in Patients With Type 2 Diabetes" (Oral Presentation), Diabetes 2012 61; A90: 346-OR.

Moore, et al, "Novel PEGylated Basal Insulin LY2605541 Has a Preferential Hepatic Effect on Glucose Metabolism", Diabetes vol. 63 pp. 494-504 (2014).

Rolla, "Pharmacokinetic and Pharmacodynamic Advantages of Insulin Analogues and Premixed Insulin Analogues Over Human Insulins: Impact on Efficacy and Safety", The American Journal of Medicine, 121(6a), S9-S19 (Jun. 2008).

Hartman, "Insulin Analogs: Impact on Treatment Success, Satisfaction, Quality of Life, and Adherence", Clinical Medicine & Research, 6(2), 54-67 (2008).

Moore, M. C., Smith, M. S., Sinha, V. P., Beals, J. M., Michael, M. D., Jacober, S. J., and Cherrington, A. D. (2013)"Basal Insulin LY2605541 Has Hepato-Preferential Action Across a Range of Delivery Rates.", Diabetes July; 62, Supplement 1, A231.

Topp, B. G., Geiser, J. S., Soon, D. K. W., Heise, T., Dodson, M. D., Jacober, S. J., Beals, J. M., Sinha, V. P. (2013) "Effects of a Novel Basal Insulin, LY2605541, on Hepatic Glucose Output and Muscle Glucose Uptake: A Physiologic Based Simulation Analysis.", Diabetes July; 62, Supplement 1, A231LY2605541: Leveraging Hydrodynamic size to Develop a Novel Basal Insulin, American Diabetes Association Jun. 2012.

Hansen R.J., Cutler, G.B., Vick, A., Koester, A., Li, S., Siesky, A.M., Beals, J.M. (2012) LY2605541: Leveraging Hydrodynamic Size to Develop a Novel Basal Insulin., Diabetes June vol. 61, Supplement 1, A228.

Jacober, S.J., Rosenstock, J., Bergenstal, R.M., Prince, M.J., Qu, Y., Beals, J.M. (2012) "Contrasting Weight Changes With LY2605541, a Novel Long-Acting Insulin, and Insulin Glargine Despite Similar Improved Glycemic Control in T1D and T2D", Diabetes June vol. 61, Supplement 1, A262.

Moore, M.C., Smith, M.S., Mace, K.F., Sinha, V.P., Michael, M.D., Jacober, S.J., Beals, J.M., Cherrington, A.D., "Novel Pegylated Basal insulin LY2605541 Has a Preferential Hepatic Effect on Glucose Metabolism", Diabetes June vol. 61, Supplement 1, A417.

Owens, R.A., Lockwood, J.F., Dunbar, J.D., Zhang, C., Ruan, X., Kahl, S.D., and Beals, J.M. (2012) In Vitro Characterization of Novel Basal Insulin LY2605541: Reduced Mitogenicity and IGF-IR Binding., Diabetes June vol. 61, Supplement 1, A425.

Kohn WD, Micanovic R, Myers SL, Vick AM, Kahl SD, Zhang L, Strifler BA, Li S, Shang J, Beals JM, Mayer JP, DiMarchi RD. (2007) "pl-shifted insulin analogs with extended in vivo time action and favorable receptor selectivity." Peptides 28(4) 935-48.

Varshavsky, A. D., Birnbaum, D. T., Beals J. M., and Saxberg, B.E.H. (2000) "Global stochastic optimization in hierarchical modeling of ligand/protein binding profiles", Kybernetes 29(4), 452-472.

Birnbaum, D. T., Kilcomons, M. A., DeFelippis, M. R., and Beals, J. M. (1997) "Hexameric kinetics of association and dissociation of a fast acting insulin analog: LysB28ProB29-insulin", Pharmaceutical Research 14, 25-36.

Bakaysa, D. L., Beals, J. M., Brader, M. L., Dodd, S. W., Edwards, S. L., Havel, H. A., Radziuk, J., and Brems, D. N. (1996) "Physicochemical basis for the rapid time-action of LysB28ProB29-insulin: Dissociation of a protein-ligand complex", Protein Science 5, 2521-2531.

Birnbaum, D. T., Dodd, S. W., Saxberg, B. E. H., Varshaysky, A. D., and Beals, J. M. (1996) "Hierarchical modeling of phenolic ligand binding in 2Zn-insulin hexamers", Biochemistry 35, 5366-5378.

Ciszak, E., Beals, J. M., Frank, B. H., Baker, J. C., Carter, N. D., and Smith, G. D. (1995) "Role of C-terminal B-chain residues in insulin assembly: The structure of hexameric LysB28ProB29-human insulin", Structure 3, 615-622.

Dodd, S. W., Havel, H. A., Kovach, P. M., Lakshminarayen, C., Redmon, M. P., Sargeant, C. M., Sullivan, G. R., and Beals, J. M. (1995) "Reversible adsorption of soluble hexameric insulin onto the surface of insulin crystals cocrystallized with protamine: An electrostatic interaction", Pharmaceutical Research 12, 60-68.

Hardaway, L. A., Brems, D. N., Beals, J. M., and McKenzie, N. E. (1994) "Amide hydrogen exchange of the central B-chain helix within the T & R states of insulin hexamers", Biochim. Biophys. Acta 1208, 101-103.

Lilly's Basal Insulin Peglispro Shows Superiority in HbA1c Reduction Compared to Insulin Glargine in Three Phase III Trials in Patients With Type 2 Diabetes, Lilly expects U.S. and European regulatory submissions by Q1 2015, Eli Lilly and Company Press Release Archives, May 12, 2014, http://lilly.mediaroom.com/index.php?s=9042&item=137302.

(56) References Cited

OTHER PUBLICATIONS

Heise and Meneghini, "Insulin Stacking Versus Therapeutic Accumulation: Understanding the Differences", Endocrine Practice, vol. 20, No. 1, Jan. 2014.
Still, "Development of oral insulin: progress and current status", Diabetes/Metabolism Research and Reviews, 18 (Suppl 1), S29-S37 (2002).
Webster, et al., "PEGylated Proteins: Evaluation of Their Safety in the Absence of Definitive Metabolism Studies", Drug Metabolism and Disposition, vol. 35, No. 1, pp. 9-16, (2007).
Sinha, et al., "Steady-state pharmacokinetics and glucodynamics of the novel, long-acting basal insulin LY2605541 dosed once-daily in patients with type 2 diabetes mellitus", Diabetes, Obesity and Metabolism, 16: pp. 344-350 (2014).

* cited by examiner

SEQUENCE LISTING

```
<160> NUMBER OF SEQ ID NOS: 6

<210> SEQ ID NO 1
<211> LENGTH: 21
<212> TYPE: PRT
<213> ORGANISM: HOMO SAPIENS

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: HOMO SAPIENS

<400> SEQUENCE: 2

Phe Val Asn Gln His Leu Cys Gly Ser His Leu Val Glu Ala Leu Tyr
1               5                   10                  15
```

```
Leu Val Cys Gly Glu Arg Gly Phe Phe Tyr Thr Pro Lys Thr
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic Construct

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 4
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is absent, any basic amino
      acid, or any genetically encodeable amino acid
<220> FEATURE:
<221> NAME/KEY: MISC_FEATURE
<222> LOCATION: (22)..(22)
<223> OTHER INFORMATION: Xaa at position 22 is absent, Gly, Ser, Ala, or
      Asn

<400> SEQUENCE: 4

Xaa Gly Ile Val Glu Gln Cys Cys Thr Ser Ile Cys Ser Leu Tyr Gln
1               5                   10                  15

Leu Glu Asn Tyr Cys Xaa
            20

<210> SEQ ID NO 5
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is absent, any basic amino
      acid, or any genetically encodeable amino acid
<220> FEATURE:
<221> NAME/KEY: MISC_FEATURE
<222> LOCATION: (29)..(29)
<223> OTHER INFORMATION: Xaa at position 29 is Pro, Asp, Lys, Leu, Val,
      or Ala
<220> FEATURE:
<221> NAME/KEY: MISC_FEATURE
<222> LOCATION: (30)..(30)
<223> OTHER INFORMATION: Xaa at position 30 is Lys or Pro
<220> FEATURE:
<221> NAME/KEY: MISC_FEATURE
<222> LOCATION: (31)..(31)
<223> OTHER INFORMATION: Xaa at position 31 is absent or Thr
<220> FEATURE:
<221> NAME/KEY: MISC_FEATURE
<222> LOCATION: (32)..(32)
<223> OTHER INFORMATION: Xaa at position 32 is absent
<220> FEATURE:
<221> NAME/KEY: MISC_FEATURE
<222> LOCATION: (33)..(33)
<223> OTHER INFORMATION: Xaa at position 33 is absent
```

```
<400> SEQUENCE: 5

Xaa Phe Val Asn Gln His Leu Cys Gly Ser His Leu Val Glu Ala Leu
1               5                   10                  15

Tyr Leu Val Cys Gly Glu Arg Gly Phe Phe Tyr Thr Xaa Xaa Xaa Xaa
            20                  25                  30

Xaa

<210> SEQ ID NO 6
<211> LENGTH: 33
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 is absent, or any genetically
      encodeable amino acid
<220> FEATURE:
<221> NAME/KEY: MISC_FEATURE
<222> LOCATION: (29)..(29)
<223> OTHER INFORMATION: Xaa at position 29 is Pro, Asp, Lys, Leu, Val,
      or Ala
<220> FEATURE:
<221> NAME/KEY: MISC_FEATURE
<222> LOCATION: (30)..(30)
<223> OTHER INFORMATION: Xaa at position 30 is Lys or Pro
<220> FEATURE:
<221> NAME/KEY: MISC_FEATURE
<222> LOCATION: (31)..(31)
<223> OTHER INFORMATION: Xaa at position 31 is absent or Thr
<220> FEATURE:
<221> NAME/KEY: MISC_FEATURE
<222> LOCATION: (32)..(32)
<223> OTHER INFORMATION: Xaa at position 32 is absent
<220> FEATURE:
<221> NAME/KEY: MISC_FEATURE
<222> LOCATION: (33)..(33)
<223> OTHER INFORMATION: Xaa at position 33 is absent

<400> SEQUENCE: 6

Xaa Phe Val Asn Gln His Leu Cys Gly Ser His Leu Val Glu Ala Leu
1               5                   10                  15

Tyr Leu Val Cys Gly Glu Arg Gly Phe Phe Tyr Thr Xaa Xaa Xaa Xaa
            20                  25                  30

Xaa
```

PEGYLATED INSULIN LISPRO COMPOUNDS

The present invention relates to the field of diabetes. More particularly, the invention relates to PEGylated insulin lispro compounds that are highly soluble and have an extended profile of action, to methods of providing such molecules, to pharmaceutical compositions containing them, and to the therapeutic use of such compounds.

In order to achieve normal glycemia, insulin replacement therapy is designed to parallel as closely as possible the pattern of endogenous insulin secretion in normal individuals. The daily physiological demand for insulin fluctuates and can be separated into two phases: (a) the absorptive phase requiring a pulse of insulin to dispose of the meal-related blood glucose surge, and (b) the post-absorptive phase requiring a sustained amount of insulin to regulate hepatic glucose output for maintaining optimal fasting blood glucose. Accordingly, effective insulin therapy for diabetics generally involves the combined use of two types of exogenous insulin formulations: a rapid-acting, mealtime insulin provided by bolus injections, and a longer-acting insulin, administered by injection once or twice daily to control blood glucose levels between meals.

Currently available insulin replacement therapies are deficient in one or more clinically important aspects. For example, traditional intermediate- and long-acting insulin formulations, such as the basal insulin analog, insulin detemir, possess a duration of activity that is insufficient to provide basal glucose control for a full day when administered daily. As a result, the duration of action of basal insulin is oftentimes insufficient to adequately control hyperglycemia and, more specifically, post-adsorptive phase requirements, with a single daily injection. Furthermore, the omission of a single injection of the current therapies can lead to significant increase in "peak-to-trough" levels of the drug resulting in impaired glucose control. Moreover, the utilization of insolubility strategies to prolong insulin release in traditional intermediate- and long-acting insulin formulations, e.g., crystalline suspensions of Neutral Protamine Hagedorn (NPH) insulin and ULTRALENTE®, or the in vivo precipitation strategy of insulin glargine, increase intra-injection variability resulting in increased variability in the dose-response profile. More specifically, NPH and ULTRALENTE® suspensions require mechanical mixing to insure product uniformity, have increased intra-subject variability, and tend to peak rather than provide an ideal "flat" pharmacodynamic profile necessary to maintain optimal fasting blood glucose for an extended period of time between meals. Therefore, insulin formulations that rely on a insoluble state to protract insulin payout are inherently less predictable than soluble formulations and result in less than adequate control of blood glucose and a greater susceptibility to life-threatening hypoglycemic episodes. Additionally, modern basal insulin analogs are not readily mixable with rapid- or immediate-acting insulin formulations. Thus, current insulin replacement therapies still leave diabetic patients susceptible to life-threatening hypoglycemic episodes, the serious long-term medical complications of diabetes and/or impose considerable inconvenience and quality-of-life disadvantages to the patient.

U.S. Pat. No. 4,179,337 entitled "Non-Immunogenic Polypeptides" discloses insulin conjugated to linear PEG molecules having a molecular weight of between about 500 and about 20,000 Da. Hinds and Kim disclosed insulin conjugated with low molecular weight (600 Da, 750 Da, and 2000 Da) monomethoxypoly(ethlene glycol) (Hinds, K. D., and Kim, et al., *Advanced Drug Delivery Reviews*, 54:505-530 (2002)). In that article, the authors stated that they restricted their study to low-molecular weight mPEG insulin conjugates "because the attachment of higher-molecular-weight mPEG (5000 Da) was [previously] found to considerably depress the conjugate's bioactivity." PCT International Patent Application Publication No. WO 2006/079641 discloses the conjugation of insulin derivatives, including insulin lispro, with small branched polymers. PCT International Patent Application Publication No. WO 2004/091494 discloses, inter alia, insulin molecules conjugated to linear and branched PEG molecules having a total molecular weight of PEG up and about 10 kDa and about 20 kDa, respectively. PCT International Patent Application Publication Nos. WO 2008/015099 (published 7 Feb. 2008) and WO 2008/084051 (published 17 Jul. 2008) disclose, inter alia, various insulin analogs conjugated to PEG molecules having a nominal molecular weight in the range from about 200 to about 40,000 Da.

Clearly, there still exists a critical need for long-lasting insulins that are better suited for basal insulin replacement regimens. In particular, soluble basal insulins that are mixable with prandial insulin formulations, have extended time-action profiles (i.e., able to adequately control blood glucose levels with an once-daily or less frequent injection), flatter activity, pharmacokinetic profiles (i.e., lower "peak-to-trough" ratios), reduced intra-patient variability (i.e., more predictable time-action profile translating into reduced incidence of hypoglycemia and/or weight gain) and/or lesser injection site irritation or pain upon injection are needed.

We report here the discovery that insulin lispro can be PEGylated with high molecular weight poly(ethylene glycol) derivatives to provide PEGylated insulin lispro compounds that have therapeutically effective basal insulin activity, extended time-action profiles, are highly soluble at physiological pH, and/or are mixable with other commonly used prandial insulin formulations.

The present invention provides a compound of Formula I: P-[(A)-(B)], or a pharmaceutically acceptable salt thereof, wherein:

A is the A-chain of insulin lispro (SEQ ID NO: 1);
B is the B-chain of insulin lispro (SEQ ID NO: 3); and
P is a PEG having a molecular weight in the range from about 20 kDa to about 40 kDa, and wherein the A and B are properly cross-linked and P is attached either directly or indirectly via a covalent bond to the alpha-amino group of the glycine at position 1 of A, the alpha-amino group of the phenylalanine at position 1 of B, or the epsilon-amino group of the lysine at position 28 of B.

The present invention also provides compositions comprising a plurality of mono- and di-PEGylated insulin lispro compounds wherein greater than about 75% of the PEGylated insulin lispro compounds in the composition are mono-PEGylated compounds of Formula I.

The present invention also provides compositions comprising mono-PEGylated insulin compounds of Formula I wherein greater than about 50% of the mono-PEGylated compounds in the composition have a PEG covalently attached either directly or indirectly to the epsilon-amino group of the lysine at position 28 of the B-chain.

The present invention also provides pharmaceutical compositions comprising a PEGylated insulin lispro of Formula I and one or more pharmaceutically acceptable preservatives, isotonicity agents, metal ions, or buffers. In certain embodiments of the invention, pharmaceutical compositions comprising a PEGylated insulin lispro of Formula I and one or more pharmaceutically acceptable preservatives, isotonicity agents, metal ions, or buffers further comprise a therapeutically effective amount of an insulin analog.

The present invention also provides methods of treating hyperglycemia, diabetes mellitus or gestational diabetes comprising administering to a patient a therapeutically effective amount of a pharmaceutical composition comprising a PEGylated insulin lispro compound of the present invention.

The present invention also includes the use of a PEGylated insulin lispro compound of the present invention for therapy.

The present invention also includes the use of a PEGylated insulin lispro compound of the present invention for the manufacture of a medicament for the treatment of hypoglycemia, diabetes mellitus, or gestational diabetes.

DETAILED DESCRIPTION OF THE INVENTION

Figure 1:
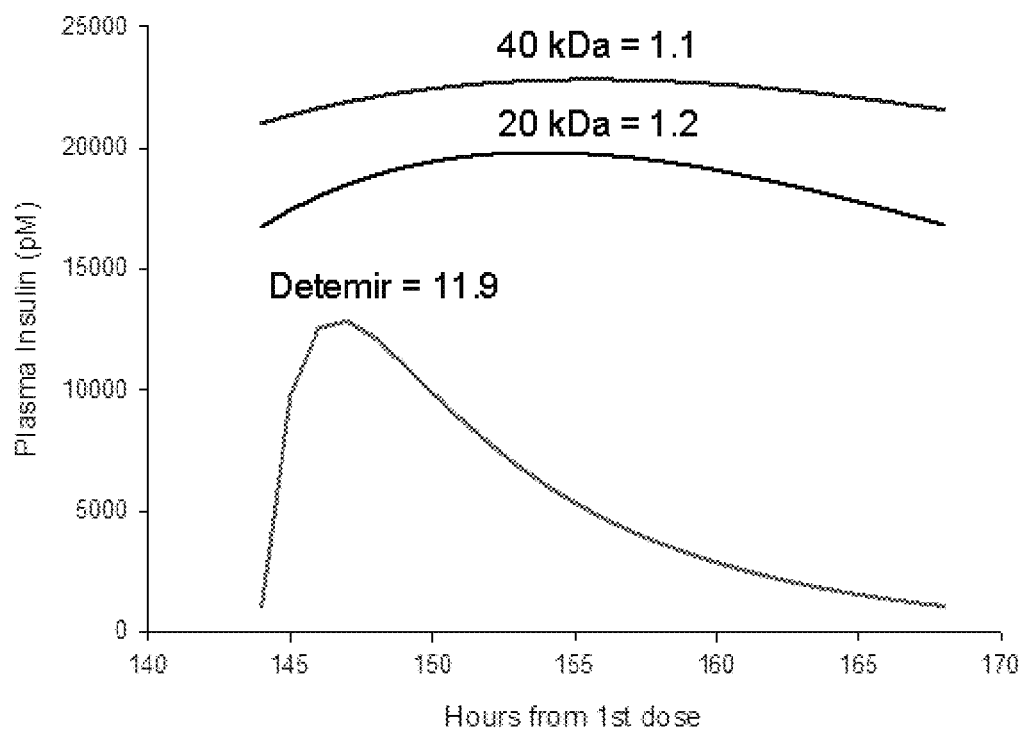
FIG. 1 graphically depicts simulated human PK profiles for 20 kDa PEG-B28-insulin lispro, 40 kDa-PEG-B28-insulin lispro, and insulin detemir, based on allometric scaling of PK parameters from rats and dogs. Profiles represent one dosing interval following a week of dosing. Numbers are mean peak-trough ratios.

The following abbreviations are used herein: ACN: Acetonitrile. Boc: tert-Butoxycarbonyl. BSA: bovine serum albumin. DCM: dichloromethane, methylenechloride. DMF: N,N-dimethylformamide. DMSO: Di-methyl sulphoxide. DTT: Dithiothreitol. EDTA: ethylenediamine tetraacetic acid. Et: Ethyl. EtOH: Ethanol. Fmoc: 9-Fluorenylmethyloxycarbonyl. HCl: Hydrochloric acid. Da: Dalton. kDa: kilodalton. Lilly: Eli Lilly and Company (Indianapolis, Ind.). mAb: monoclonal antibody. Me: Methyl. MeOH: Methanol. PBS: phosphate-buffered saline. RP-HPLC: reversed-phase high-performance liquid chromatography. SEC: size-exclusion chromatography. SEM: standard error of the mean. SPA: scintillation proximity assay. TFA: trifluoroacetic acid. All amino acid abbreviations used in this disclosure are those accepted by the United States Patent and Trademark Office as set forth in 37 C.F.R. §1.822(B)(2).

The term "insulin" is intended to encompass wild-type insulin from any species including, but not limited to, porcine insulin, bovine insulin, and human insulin. Native or wild-type insulin refers to insulin having an amino acid sequence corresponding to the amino acid sequence of insulin as found in nature. Polynucleotide and amino acid sequences encoding insulin from a number of different species are well known to those of ordinary skill in the art. For example, human insulin has a twenty-one amino acid A-chain and a thirty amino acid B-chain (SEQ ID NOS: 1 and 2, respectively). Insulin can be natural (i.e., isolated from a natural source), biosynthetically, or synthetically produced. The term "insulin" is also intended to include any insulin derivative and/or insulin analog.

An "insulin analog" or "insulin derivative" is defined herein as protein having insulin activity and substantially the same amino acid sequence as human insulin but differing from human insulin by a modification relative to human insulin including one or more amino acid substitutions, deletions, inversions, or additions. Such compounds are well known in the art. See, e.g. PCT International Patent Application Publication Nos. WO 96/15804 and WO 03/053339; U.S. Pat. Nos. 3,528,960, 5,514,646, 5,618,913, 5,750,497, 6,011,007, 6,251,856; and EP Patent Nos. 254,516 and 280,534. An exemplary but non-exhaustive list of insulin analogs known to one skilled in the art includes insulin aspart, insulin lispro, insulin glargine, insulin detemir, and insulin glulisine. Furthermore, the term "insulin" herein also covers compounds which can be considered as being both an insulin derivative and an insulin analog. Examples of such compounds are described in the U.S. Pat. Nos. 5,750,497, and 6,011,007. A specific example of such a compound known to one skilled in the art is insulin detemir.

Various insulin analogs and/or derivatives are known to be "fast-acting" or "rapid-acting" insulin analogs. The terms "fast-acting" and "rapid-acting" are used interchangeably herein. A "rapid-acting insulin analog" produces a prandial glucose effect that (a) begins sooner after subcutaneous administration than human insulin, and/or (b) exhibits a shorter duration of action than human insulin after subcutaneous administration. Exemplary fast-acting insulin analogs include "monomeric insulin analogs" that are fast-acting because they are generally less prone to dimerization or self-association under physiological conditions. Monomeric insulin analogs are known in the art. See, e.g., U.S. Pat. No. 5,700,662, and European Patent No. 214 826. Insulin lispro is a rapid-acting, monomeric insulin analog in which the proline at position 28 of the wild-type insulin B-chain (SEQ ID NO: 2) and the lysine at position 29 of the wild-type insulin B-chain (SEQ ID NO: 2) have been switched. Accordingly, insulin lispro is known in the art by various designations including, but not limited to, $Lys^{B28}Pro^{B29}$-human insulin, LysB28ProB29-human insulin, and B28Lys, B29Pro human insulin.

The term "cross-linked" means disulfide bonds exist between cysteine residues. For instance, properly cross-linked human insulin contains a disulfide bond between the cysteine at position 7 of SEQ ID NO: 1 and the cysteine at position 7 of SEQ ID NO: 2, between the cysteine at position 20 of SEQ ID NO: 1 and the cysteine at position 19 of SEQ ID NO: 2, and between the cysteine at position 6 of SEQ ID NO: 1 and the cysteine at position 11 of SEQ ID NO: 1. Similarly, a properly cross-linked insulin lispro compound contains a disulfide bond between the cysteine at position 7 of SEQ ID NO: 1 and the cysteine at position 7 of SEQ ID NO: 3, between the cysteine at position 20 of SEQ ID NO: 1 and the cysteine at position 19 of SEQ ID NO: 3, and between the cysteine at position 6 of SEQ ID NO: 1 and the cysteine at position 11 of SEQ ID NO: 1.

As used herein, "PEG conjugated insulin lispro" or "PEGylated insulin lispro" refers to human insulin lispro or a derivative thereof covalently attached to at least one PEG and possessing insulin activity in vivo.

The biological activities of insulin and insulin lispro are well-established. The phrase "insulin activity" with respect to a PEGylated insulin lispro compound of the present invention is intended to mean the ability to significantly lower blood glucose levels in at least one generally accepted in vivo animal model including, but not limited to, the animal models of Type 1 and Type 2 diabetes described below in Example 5 and Example 6, respectively. Therefore, insulin activity includes the ability of a PEGylated insulin lispro compound to lower blood glucose to a level of 100 mg/dL or below in a STZ-treated rat for a period ranging from about 4 hours to at least about 36 hours after a single subcutaneous injection at a dose of 568 nmol/kg.

The term "polyethylene glycol" or "PEG" refers to a polyalkylene glycol compound or derivative thereof, with or without coupling agents or derivatization with coupling or activating moieties. In its typical form, PEG is a linear polymer with terminal hydroxyl groups and has the formula HO—CH$_2$CH$_2$—(CH$_2$CH$_2$O)$_n$—CH$_2$CH$_2$—OH. The number of repeating subunits "n" in the PEG is approximated for the molecular mass described in Daltons. Typically, PEG reagents used to prepare PEGylated compounds comprise a heterogenous mixture of PEGs having a different number (n) of ethylene glycol subunits in the PEG polymer. A single ethylene glycol subunit (—(CH$_2$CH$_2$O)) of PEG has a molecular weight of about 44 Daltons. Therefore, the molecular weight of the PEG polymer depends on the number (n). The PEGs attached to the PEGylated insulin lispro compounds of the present invention will have n in the range from about 400 to about 1000 subunits. Preferably, the PEGs attached to the PEGylated insulin lispro compounds of the present invention will have n in the range from about 400 to about 750. More preferably, the PEGs attached to the PEGylated insulin lispro compounds of the present invention will have n in the range from about 400 to about 550. Most preferably, the PEGs attached to the PEGylated insulin lispro compounds of the present invention will have n of about 400 and about 500.

Numerous derivatives of PEG and methods for making them and conjugating them to a protein such as insulin or insulin lispro are known in the art and are suitable for use in the present invention. See, e.g. PCT International Patent Application Pub. Nos. WO 01/62827, WO 2006/028745, WO 2006/096535, WO 2006/036825; Zalipsky, S. *Bioconjugate Chem.* 6:150-165, 1995; Veronese, et al., *Applied Biochem. and Biotech.* 11:141-152, 1985; and Roberts, M. et al. *Advanced Drug Delivery Reviews,* 54:459-476, 2002. One particularly preferred PEG for use in the invention is a PEG having one end of the polymer terminating with a relatively inert group, such as a lower C$_{1-6}$ alkoxy group. Preferably, the PEG is a monomethoxy-PEG (commonly referred to as mPEG), which is a linear form of PEG wherein one terminus of the polymer is a methoxy (—OCH$_3$) group. Even more preferably, the PEG used in the invention is an "activated mPEG" in which one end of the linear PEG terminates with a methoxy group and the other end terminates with a reactive group appropriate for coupling to a desired site on insulin lispro or on an insulin lispro derivative derivatized in order to facilitate PEGylation with a desired activated mPEG at a specific site of the insulin lispro molecule.

Because PEGs are typically generated and used as mixtures of PEG compounds varying to some degree in their molecular weight, one of ordinary skill in the art generally describes the molecular weight of a PEG attached to a compound by describing the average size of the PEG reagent used in the PEGylation reaction that generated the particular PEGylated compound. Among the many possible ways of reporting averages, three are commonly used: the number average, weight average, and z-average molecular weights. As used herein, the phrase "average molecular weight" is intended to refer to the weight-average molecular weight which can be measured using techniques well-known in the art including, but not limited to, matrix-assisted laser desorption ionization time of flight (MALDI-TOF) mass spectrometry, gel permeation chromatography or other liquid chromatography techniques, light scattering techniques, ultracentrifugation and viscometry. The formula for calculating weight average molecule weight may be represented as $\Sigma(M_i^2 N_i)/\Sigma(M_i N_i)$ where $N_i$ is the mole-fraction (or the number-fraction) of molecules with molecular weight $M_i$ in the mixture. The formula for calculating number average molecule weight may be represented as $\Sigma(M_i N_i)/\Sigma(N_i)$ where $N_i$ is the mole-fraction (or the number-fraction) of molecules with molecular weight $M_i$ in the mixture. The ratio of weight average molecular weight and number average molecular weight is known as the polydispersity index (PDI), and provides a rough indication of the breadth of the distribution. The PEG reagents suitable for preparing the PEGylated insulin lispro compounds of the invention are typically polydisperse (i.e., number average molecular weight and weight average molecular weight of the polymers are not equal). Preferably, the PDI for PEG reagents used to prepare the compounds or compositions of the present invention is less than about 1.1. More preferably, the PDI for PEG reagents used to prepare the compounds or compositions of the present invention is less than about 1.05.

With respect to the PEGylated insulin lispro compounds of the present invention the PEG covalently attached to an insulin lispro molecule has a molecular weight in the range from about 17.5 kDa to about 40 kDa (n is in the range from about 400 to about 1000) or the PEG has an average molecular weight of about 17.5 kDa and about 40 kDa. Preferably, the PEG covalently attached to an insulin lispro molecule has a molecular weight in the range from about 20 kDa to about 30 kDa (n is in the range from about 450 to about 750) or the PEG has an average molecular weight from about 20 kDa to about 30 kDa. More preferably, the PEG covalently attached to an insulin lispro molecule has a molecular weight in the range from about 17.5 kDa to about 25 kDa (n is in the range from about 400 to about 550) or the PEG has an average molecular weight of about 17.5 kDa and about 25 kDa. Most preferably, the PEG covalently attached to an insulin lispro molecule has a molecular weight in the range from about 17.5 kDa to about 20 kDa (n is in the range from about 400 to about 500) or the PEG has an average molecular weight from about 17.5 kDa to about 20 kDa.

In certain embodiments, the PEGylated insulin lispro compounds of the present invention are prepared by covalently attaching an activated mPEG of a desired average molecular weight to insulin lispro. The reaction conditions for PEGylating insulin lispro will vary depending upon the particular PEG employed, the site of attachment on the insulin lispro, the particular type of reactive group on the insulin lispro that is the target for attachment, the desired degree of PEGylation, and the like, and can readily be determined by one skilled in the art. Optimized experimental conditions for a particular PEGylation strategy can readily be determined, typically by routine experimentation, by one skilled in the art.

In preferred embodiments, the PEGylated insulin lispro compounds of the present invention are prepared by indirectly conjugating an activated mPEG that is relatively thiol-selective such as a mPEG-maleimide (mPEG-MAL) or a mPEG-thiol (mPEG-SH) to insulin lispro by conjugating the thiol-selective activated mPEG to a thiol functionality that has been introduced into insulin lispro using "amine-to-thiol" modifiers such as N-succinimidyl-S-acetylthiopropionate (SATP) and N-succinimidyl-S-acetylthioacetate (SATA). More preferably, the activated mPEG employed to covalently attach a PEG to a thiol (sulfhydryl) group on insulin lispro is a mPEG-maleimide such as (a), (b), or (c) shown below.

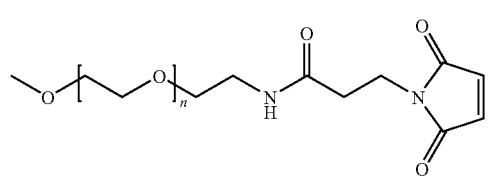

(a)

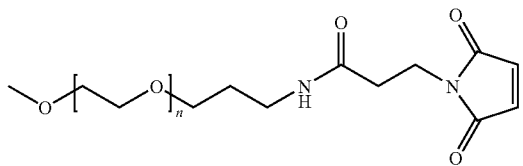

(b)

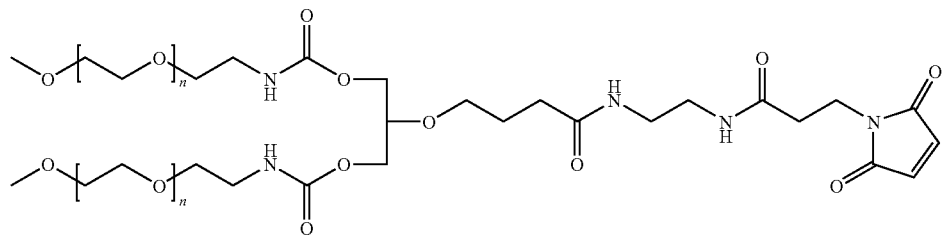

(c)

A preferred method of preparing PEGylated insulin lispro compounds of the present invention utilizes Michael addition to form a stable thioether bond. The reaction is highly specific and takes place under mild conditions in the presence of other functional groups. For example, mPEG-maleimide is useful as an activated mPEG for preparing PEGylated insulin lispro conjugates of the present invention. Preferably, the PEGylation procedure uses a molar excess of a thiol-derivatized insulin lispro relative to mPEG-maleimide to drive the reaction to completion. Preferably, the reactions are also performed between pH 4.0 and 9.0 at room temperature for 1 to 40 hours. The excess of unPEGylated thiol-containing peptide is readily separated from the PEGylated product by conventional separation methods. Exemplary conditions required for PEGylation of insulin lispro using activated mPEG-maleimide are described in Example 1.

In certain embodiments, the PEGylated insulin lispro compounds of the present invention are prepared by conjugating an activated mPEG that is relatively specific for amines. Activated mPEGs suitable for primarily amine specific PEGylation of insulin lispro include mPEG-succinimidyl propionate (mPEG-SPA), mPEG succinimidyl butanoate (mPEG-SBA), mPEG-succinimidyl α-methylbutanoate (mPEG-SMB), mPEG-succinimidyl carbonate (mPEG-SC), mPEG-benzotriazole carbonate, and mPEG-p-nitrophenyl carbonate (mPEG-NPC).

In preferred embodiments of the invention, the activated mPEGs used for PEGylation of insulin lispro result in an insulin lispro covalently attached to a mPEG through a hydrolytically stable covalent bond, such as an amide, urethane (also known as a carbamate), amine, thioether (also known as sulfide), or urea (also known as carbamide) bond. More preferably, the activated mPEG used for PEGylation of insulin lispro is mPEG-SC or mPEG-NPC, both of which result in an insulin lispro being covalently attached to the PEG through a urethane (or carbamate) bond. Exemplary conditions useful for PEGylation of insulin lispro using mPEG-NPC of various molecular weights are set forth in Example 2.

mPEG-SC:

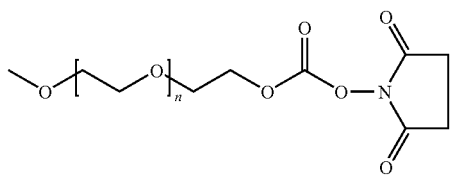

mPEG-NPC:

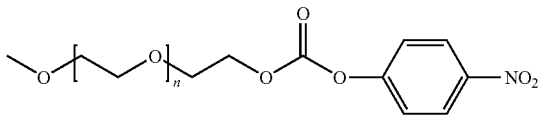

The PEGylated insulin lispro compounds of the invention are typically purified using one or more purification techniques such as ion exchange chromatography, size exclusion chromatography, affinity chromatography, hydrophobic interaction chromatography, and/or reversed-phase chromatography. The overall heterogeneity of PEGylated insulin lispro compounds (number and proportion of PEGylated insulin lispro compounds generated from a PEGylation reaction) in a sample can be assessed using one or more of the following methods: chromatography, electrophoresis, mass spectrometry, and in particular, MALDI-MS, and NMR spectroscopy.

The insulin lispro used to prepare the PEGylated insulin lispro compounds of the present invention may be prepared by any of a variety of recognized peptide synthesis techniques including solution-phase methods, solid-phase methods, semi-synthetic methods, and recombinant DNA methods. For example, U.S. Pat. No. 5,700,662 (Chance, et al.) and European Patent No. 214 826 (Brange, et al.), disclose the preparation of various insulin analogs. The A- and B-chains of insulin lispro may also be prepared via a proinsulin-like precursor molecule using recombinant DNA techniques. In preferred embodiments, a proinsulin-like precursor is used to make the insulin lispro used to make the PEGylated insulin lispro of the present invention.

The present invention provides a compound of Formula I: P-[(A)-(B)], or a pharmaceutically acceptable salt thereof, wherein:

A is the A-chain of insulin lispro (SEQ ID NO: 1);
B is the B-chain of insulin lispro (SEQ ID NO: 3); and
P is a PEG having a molecular weight in the range from about 17.5 kDa to about 40 kDa, and wherein A and B are properly cross-linked and P is attached either directly or indirectly via a covalent bond to the alpha-amino group of the glycine at position 1 of the A-chain, the alpha-amino group of the phenylalanine at position 1 of the B-chain, or the epsilon-amino group of the lysine at position 28 of the B-chain. Preferred compounds of the invention are those in which (a) P is covalently attached to insulin lispro via a urethane or thioether bond; and (b) the compound is characterized by having a Ki for human insulin receptor of about 30 nM, about 20 nM, about 10 nM, or about 5 nM or less, an elimination half-life greater than about 6 hours, about 8 hours, about 10 hours, about 12 hours, or about 14 hours in a STZ-treated rat dosed at about 568 nmol/kg, or by the activity of lowering blood glucose to a level of about 100 mg/dL or below in a STZ-treated rat for a period ranging from about 4 hours to at least about 36 hours, about 48 hours, about 60 hours, about 72 hours, about 84 hours, about 96 hours, about 108 hours, or about 120 hours after a single subcutaneous injection of the compound at a dose of about 568 nmol/kg. Even more preferred compounds are those in which: (a) P is covalently attached to insulin lispro via a urethane bond; (b) the compound is characterized by having a Ki for the human insulin receptor of about 10 nM or less; (c) the compound is characterized by having an elimination half-life greater than 6 hours in a STZ-treated rat dosed at about 568 nmol/kg; and (d) the compound is characterized by the activity of lowering blood glucose to a level of about 100 mg/dL or below in a STZ-treated rat for a period ranging from about 4 hours to at least about 48 hours, about 60 hours, about 72 hours, about 84 hours, about 96 hours, about 108 hours, or about 120 hours after a single subcutaneous injection of the compound at a dose of about 568 nmol/kg. Most preferred compounds are those in which: (a) P is covalently attached to insulin lispro via a urethane bond; (b) the compound is characterized by having a Ki for the human insulin receptor of about 10 nM or less; (c) the compound is characterized by having an elimination half-life greater than 6 hours in a STZ-treated rat dosed at about 568 nmol/kg; (d) the compound is characterized by the activity of lowering blood glucose to a level of about 100 mg/dL or below in a STZ-treated rat for a period ranging from about 4 hours to at least about 48 hours, about 60 hours, about 72 hours, about 84 hours, about 96 hours, about 108 hours, or about 120 hours after a single subcutaneous injection of the compound at a dose of about 568 nmol/kg, and (e) the compound is characterized by having an elimination half-life greater than about 24 hours, about 30 hours, about 32 hours, about 34 hours, about 36 hours, 38 hours, about 40 hours, or about 42 hours in a human upon administration of a single parenteral dose at 0.225 mg/kg.

According to features and principles consistent with the invention, an embodiment of the invention provides a mono-PEGylated insulin lispro compound comprising a PEG having an average molecular weight of about 17.5 kDa, about 20 kDa, about 25 kDa, about 30 kDa, or about 40 kDa covalently attached directly or indirectly to the alpha-amino group of glycine at position 1 of the A-chain of insulin lispro (PEG-GlyA1 insulin lispro), the alpha-amino group of the phenylalanine at position 1 of the B-chain of insulin lispro (PEG-PheB1 insulin lispro), or the epsilon-amino group of the lysine at position 28 of the B-chain of insulin lispro (PEG-LysB28 insulin lispro). Preferably, the mono-PEGylated insulin lispro comprises a PEG having an average molecular weight of about 17.5 kDa, about 20 kDa, about 25 kDa, about 30 kDa, or about 40 kDa attached either directly or indirectly to the alpha-amino group of phenylalanine at position 1 of the B-chain of insulin lispro or the epsilon-amino group of the lysine at position 28 of the B-chain of insulin lispro. More preferably, the mono-PEGylated insulin lispro comprises a PEG having an average molecular weight of about 17.5 kDa, about 20 kDa, about 25 kDa, about 30 kDa, or about 40 kDa attached to the epsilon-amino group of the lysine at position 28 of the B-chain of insulin lispro. Even more preferably, the mono-PEGylated insulin lispro comprises a PEG having an average molecular weight of about 17.5 kDa or about 20 kDa attached to the epsilon-amino group of the lysine at position 28 of the B-chain of insulin lispro (20 kDa-PEG-LysB28 insulin lispro). Most preferably, the mono-PEGylated insulin lispro comprises a PEG having an average molecular weight of about 20 kDa attached to the epsilon-amino group of the lysine at position 28 of the B-chain of insulin lispro (i.e., $PEG_{20\ kDa}$-LysB28 insulin lispro)

Other embodiments of the invention provide a mono-PEGylated insulin lispro compound comprising a PEG having a molecular weight of about 17.5 kDa, about 20 kDa, about 25 kDa, about 30 kDa, or about 40 kDa covalently attached directly or indirectly to the alpha-amino group of glycine at position 1 of the A-chain of insulin lispro, the alpha-amino group of the phenylalanine at position 1 of the B-chain of insulin lispro, or the epsilon-amino group of the lysine at position 28 of the B-chain of insulin lispro. Preferably, the mono-PEGylated insulin lispro comprises a PEG having a molecular weight of about 17.5 kDa, about 20 kDa, about 25 kDa, about 30 kDa, or about 40 kDa attached either directly or indirectly to the alpha-amino group of phenylalanine at position 1 of the B-chain of insulin lispro or the epsilon-amino group of the lysine at position 28 of the B-chain of insulin lispro. More preferably, the mono-PEGylated insulin lispro comprises a PEG having a molecular weight of about 17.5 kDa, about 20 kDa, about 30 kDa, or about 40 kDa attached to the epsilon-amino group of the lysine at position 28 of the B-chain of insulin lispro. Most preferably, the mono-PEGylated insulin lispro comprises a PEG having a molecular weight of about 20 kDa attached to the epsilon-amino group of the lysine at position 28 of the B-chain of insulin lispro and the PEG-LysB28-insulin lispro is characterized by having an elimination half-life greater than about 24 hours, about 30 hours, about 32 hours, about 34 hours, about 36 hours, about 38 hours, about 40 hours, or about 42 hours in a human upon administration of a single subcutaneous dose of the composition at 0.225 mg/kg.

In another embodiment the invention provides compositions comprising a mixture of PEGylated insulin lispro compounds where attachment of the PEG occurs at different sites and/or a mixture of mono-PEGylated, di-PEGylated, and tri-PEGylated insulin lispro compounds. Exemplary compositions in accordance with the invention are those comprising more than one PEGylated-insulin lispro compound selected from the group consisting of: i) PEG-GlyA1 insulin lispro, ii) PEG-PheB1 insulin lispro, iii) PEG-LysB28 insulin lispro, iv) di-PEG-GlyA1PheB1-insulin lispro, v) di-PEG- GlyA1LysB28-insulin lispro, vi) di-PEG-PheB1LysB28-insulin lispro, and vii) di-PEG-GlyA1PheB1-insulin lispro. More preferably, compositions of the present invention comprise a mixture of PEGylated insulin lispro compounds wherein greater than about 80%, about 85%, about 90%, about 95%, or about 97% of the PEGylated insulin lispro compounds are mono-PEGylated insulin lispro compounds of Formula I. Even more preferably, compositions of the present invention comprise a mixture of PEGylated insulin lispro compounds wherein greater than about 80%, about 85%, about 90%, about 95%, or about 97% of the PEGylated insulin lispro compounds are mono-PEGylated insulin lispro compounds and less than about 20%, about 15%, about 10%, about 5%, or about 3% of the total PEGylated insulin lispro compounds are di-PEGylated. Even more preferably, compositions of the present invention comprise a mixture of PEGylated insulin lispro compounds wherein greater than about 80%, about 85%, about 90%, about 95%, or about 97% of the PEGylated insulin lispro compounds are PEG-LysB28-insulin lispro. Even more preferably, compositions of the present invention comprise a mixture of PEGylated insulin lispro compounds wherein greater than about 80%, about 85%, about 90%, about 95%, or about 97% of the PEGylated insulin lispro compounds are PEG-LysB28-insulin lispro and less than about 20%, about 15%, about 10%, about 5%, or about 3% of the total PEGylated insulin lispro compounds are PEG-GlyA1-insulin lispro. Even more preferably, compositions of the present invention comprise a mixture of PEGylated insulin lispro compounds wherein greater than about 80%, about 85%, about 90%, about 95%, or about 97% of the PEGylated insulin lispro compounds are PEG-LysB28-insulin lispro, less than about 20%, about 15%, about 10%, about 5%, or about 3% of the total PEGylated insulin lispro compounds are PEG-GlyA1-insulin lispro and less than about 10%, about 5%, or about 3% of the total PEGylated insulin lispro compounds are di-PEGylated insulin lispro compounds. Even more preferably, compositions of the present invention comprise a mixture of PEGylated insulin lispro compounds wherein about 80% of the total PEGylated insulin lispro compounds are PEG-LysB28-insulin lispro, about 10% are PEG-GlyA1-insulin lispro, and about 10% is di-PEG-GlyA1LysB28-insulin lispro. Even more preferably, compositions of the present invention comprise a mixture of PEGylated insulin lispro compounds wherein about 90% or greater of the total PEGylated insulin lispro compounds are PEG-LysB28-insulin lispro, about 5% or less are PEG-GlyA1-insulin lispro, and about 5% or less is di-PEG-GlyA1LysB28-insulin lispro. Even more preferably, compositions of the present invention comprise a mixture of PEGylated insulin lispro compounds wherein about 90% or greater of the total PEGylated insulin lispro compounds are PEG-LysB28-insulin lispro, about 5% or less are PEG-GlyA1-insulin lispro, about 5% or less is di-PEG-GlyA1LysB28-insulin lispro and wherein the PEG-LysB28-insulin lispro is characterized by having an elimination half-life greater than about 24 hours, about 30 hours, about 32 hours, about 34 hours, about 36 hours, about 38 hours, about 40 hours, or about 42 hours in a human upon administration of a single subcutaneous dose of the composition at 0.225 mg/kg. Most preferably, compositions of the present invention comprise a mixture of PEGylated insulin lispro compounds wherein about 95% or greater of the total PEGylated insulin lispro compounds are PEG-LysB28-insulin lispro, about 5% or less are PEG-GlyA1-insulin lispro, and the PEG-LysB28-insulin lispro is characterized by having an elimination half-life greater than about 24 hours, about 30 hours, about 32 hours, about 34 hours, about 36, about 38 hours, about 40 hours, or about 42 hours in a human upon administration of a single subcutaneous dose of the composition at 0.225 mg/kg.

The term "basic conditions" as used herein refers to the basicity of the PEGylation reaction. To more selectively PEGylate insulin lispro at the lysine at position 28 of the B-chain of insulin lispro, the reaction should be carried out with the alpha-amino groups of insulin lispro substantially deprotonated. In an aqueous solvent or co-solvent, basic conditions means the reaction is carried out at a pH greater than 7.0. Preferably, the PEGylation reaction is conducted at pH from about 8.5 to about 11.5. In an organic solvent, the reaction is carried out in the presence of a base with a basicity equivalent to a $pK_a$ greater than or equal to 10.75 in water.

The present invention also includes a process of making a PEGylated insulin lispro compound of the formula:

P-[(A)-(B)], or a pharmaceutically acceptable salt thereof, wherein:

A is the A-chain of insulin lispro (SEQ ID NO: 1);
B is the B-chain of insulin lispro (SEQ ID NO: 3); and
P is a PEG having a molecular weight in the range from about 20 kDa to about 40 kDa, and wherein A and B are properly cross-linked and P is attached via an urethane covalent bond to the epsilon-amino group of the lysine at position 28 of B which comprises reacting the epsilon-amino group of the lysine at position 28 of B with monomethoxypoly(ethylene glycol) p-nitrophenyl carbonate (mPEG-NPC) having a weight average molecular weight between about 20 kDa and about 40 kDa in an aqueous solvent at a pH between about 8.5 and about 11.5 and at a reaction temperature between about 25° C. and about 30° C. Preferably, the pH of the reaction is maintained between about 10.5 and about 11.1, the pegylation reaction is conducted at a temperature between about 25° C. and about 30° C. for a period of time between about 2 and about 12 hours, and the ratio of mPEG-NPC to insulin lispro is in the range between about 1.0 and about 5.0. More preferably, the weight average molecular weight of the mPEG-NPC is about 20 kDa, the pH of the reaction is maintained between about 10.5 and about 11.1, the pegylation reaction is conducted at a temperature between about 25° C. and about 30° C. for a period of time between about 2 and about 12 hours, and the ratio of mPEG-NPC to insulin lispro is in the range between about 1.0 and about 5.0. Even more preferably, the PEG:insulin lispro molar ratio is in the range between about 2.5 and about 4.5, the weight average molecular weight of the mPEG-NPC is about 20 kDa, the pH of the pegylation reaction is maintained between about 10.5 and about 11.1, the temperature of the pegylation reaction is maintained between about 25° C. and about 30° C. for a period of time between about 3 and about 6 hours. Most preferably, the PEG:insulin lispro molar ratio is in the range between about 2.6 and about 4.5, the weight average molecular weight of the mPEG-NPC is about 20 kDa, the pH of the pegylation reaction is maintained between about 10.5 and about 11.0, and the temperature of the reaction is maintained between about 25° C. and about 30° C. for about 3 hours.

If desired, PEGylated insulin lispro compounds of the present invention having different molecular weights can be isolated using various techniques known to one skilled in the art including, but not limited to, gel filtration chromatography and/or ion exchange chromatography. That is to say, gel filtration chromatography may be used to fractionate mono-PEGylated, di-PEGylated, and tri-PEGylated insulin lispro compounds on the basis of their differing molecular weights (where the difference corresponds essentially to the average molecular weight of the PEG used in the PEGylation reaction). For example, in an exemplary reaction where an insulin lispro is conjugated to an activated mPEG having an average molecular weight of about 20 kDa, the resulting reaction mixture may contain unmodified insulin lispro having a molecular weight of about 5,808 Daltons, mono-PEGylated insulin lispro having an average molecular weight of about 25,808 Daltons, di-PEGylated insulin lispro having an average molecular weight of about 45,808 Daltons kDa, and tri-PEGylated insulin lispro having an average molecular weight of about 65,808 Daltons. However, because gel filtration techniques separate compounds based on hydrodynamic size, mono-PEGylated insulin lispro conjugated to an mPEG having an average molecular weight of about 20 kDa will migrate during gel filtration as an approximately 82 kDa protein despite having an average molecular weight of about 25,808 Daltons. One skilled in the art would expect a di- and tri-PEGylated species pegylated with an average molecular weight mPEG of about 20 kDa to have very different migration or retention times allowing for their purification and/or quantification.

The phrase "plasma half-life" refers to the time taken for the plasma concentration of the drug in the body to fall by one-half. An alternatively used term is "elimination half-life", which corresponds to the terminal log-linear rate of elimination. Those of skill in the art appreciate that half-life is a derived parameter that changes as a function of both clearance and volume of distribution. The terms "extended", "longer", or "increased" used in the context of plasma half-life or elimination half-life are used interchangeably herein and are intended to mean that there is a statistically significant increase in the half-life of a test compound (e.g., a PEGylated insulin lispro) relative to that of the reference molecule (e.g., insulin lispro) as determined under comparable conditions.

Clearance is the measure of the body's ability to eliminate a drug. As clearance decreases due, for example, to modifications to a drug, half-life would be expected to increase. However, this reciprocal relationship is exact only when there is no change in the volume of distribution. A useful approximate relationship between the terminal log-linear half-life $(t_{1/2})$, clearance (CL), and volume of distribution (V) is given by the equation: $t_{1/2} \sim 0.693$ (V/CL). Clearance does not indicate how much drug is being removed but, rather, the volume of biological fluid such as blood or plasma that would have to be completely freed of drug to account for the elimination. Clearance is expressed as a volume per unit of time.

The term "treatment" or "treating" as used herein refers to the management and care of a patient having diabetes or hyperglycemia, or other condition for which insulin administration is indicated for the purpose of combating or alleviating symptoms and complications of those conditions. Treating includes administering compounds or compositions of the present invention to prevent the onset of symptoms or complications, alleviating the symptoms or complications, or eliminating the disease, condition, or disorder. The patient to be treated is a mammal, and preferably, a human being.

The PEGylated insulin lispro compounds of Formula I are effective in treating hyperglycemia by administering to a patient in need thereof a therapeutically effective amount of one or more compounds of Formula I. As used herein the phrase "therapeutically effective amount" refers to that amount of a PEGylated insulin lispro compound of Formula I or compositions thereof sufficient to regulate blood glucose in a patient. Preferably, a therapeutically effective amount of a PEGylated insulin lispro of Formula I is from about 0.01 nmol/kg to about 100 nmol/kg. More preferably, a therapeutically effective amount is from about 0.01 to about 50 nmol/kg. Even more preferably, a therapeutically effective amount is from about 0.01 to about 20 nmol/kg. Even more preferably, a therapeutically effective amount is from about 0.01 to about 10 nmol/kg. Even more, preferably a therapeutically effective amount is from about 0.1 to about 7.5 nmol/kg. Even more, preferably a therapeutically effective amount is from about 0.1 to about 5 nmol/kg. Most preferably, a therapeutically effective amount is from about 0.5 to about 5 nmol/kg. However, it is to be understood that the amount of a PEGylated insulin lispro compound or a composition comprising one or more PEGylated insulin lispro compounds actually administered will be determined by a physician in light of the relevant circumstances including the condition being treated (i.e., the cause of the hyperglycemia), the particular species of PEGylated insulin lispro or particular mixture of PEGylated insulin lispro compounds to be administered, other drugs, insulins or otherwise, to be co-administered, the chosen parenteral route of administration, the age, weight and response of the individual patient and the severity of the patient's symptoms. Therefore, the above dosage ranges are not intended to limit the scope of the invention in any manner.

The phrase "sufficient to regulate blood glucose" means that administration of a compound or composition to a patient results in a normal fasting plasma glucose level. A clinically normal fasting plasma glucose level is 70-110 mg/dL. A clinically normal postprandial plasma glucose level is less than 140 mg/dL.

Covalent chemical changes in the insulin structure are known to occur upon storage. This may lead to the formation of molecules which are less active and potentially immunogenic such as deamidation products and higher molecular weight transformation products (e.g., dimers, oligomers, polymers). A comprehensive study on the chemical stability of insulin is given in by Jens Brange in "Stability of Insulin", Kluwer Academic Publishers, 1994. The shelf-life of insulin products is mainly compromised by the formation of soluble aggregates (dimers, oligomers, and polymers) over time, despite the fact that insulin compositions are typically stored at a low temperature of no more than about 2-8° C., which improves the shelf-life considerably compared to storage, e.g., at room temperature. In addition, insulin products are subject to the formation of insoluble aggregates (fibrils) as a result of shaking, e.g., when carried in the pocket of a patient or during transport. It is essential for the quality of an insulin product that the tendency to form such soluble and insoluble aggregates as a result of chemical or physical influences is reduced to an absolute minimum. Therefore, insulin compositions must demonstrate acceptable chemical and physical stability characteristics in order to be used therapeutically.

The term "stability" as used herein refers to the physical and/or chemical stability of formulations of PEGylated insulin lispro compounds. Physical instability of a PEGylated insulin lispro formulation may be caused by aggregation of the protein molecules to form higher order polymers or even precipitates. A "stable" formulation is one where the degree of aggregation of proteins is acceptably controlled, and does not increase unacceptably with time. In certain embodiments of the invention, a PEGylated insulin lispro formulation is considered stable over a certain time period if the degree of aggregation is within about 1%, 2%, 3%, 4%, 5%, 10%, 15%, 20%, 25% or 30% of the degree of aggregation observed in the starting material. In certain embodiments of the invention, a PEGylated insulin lispro formulation is considered stable over a certain time period if the polypeptide's biological activity is at least about 99%, 95%, 90%, 85%, 80%, 75%, 70%, 65%, 60%, 55% or 50% of the activity observed with the starting material.

The term "chemical stability" as used herein refers to the tendency of a PEGylated insulin lispro composition to form soluble protein aggregates during storage under static conditions, including storage at low temperatures of approximately 2-8° C. or elevated temperatures of approximately 20-40° C. The chemical stability of a PEGylated insulin lispro compound of the invention can be measured by determining analytical attributes in the formulation under specific conditions, such as at a particular temperature and humidity condition over a certain period of time. The analytical attributes that can be measured include the formation of high molecular weight species using size-exclusion HPLC, for instance. The results can then be monitored and compared against pre-specified parameters.

The term "physical stability" as used herein refers to the tendency of a PEGylated insulin lispro composition to form insoluble protein aggregates as a result of a physical action such as shaking of a PEGylated insulin lispro composition. The physical stability of PEGylated insulin lispro compounds of the invention upon storage for a defined period of time at various temperatures in various pharmaceutical formulations may be assessed by methods well-known in the art, including measurement of a sample's apparent attenuation of light (absorbance or optical density). Such a measurement of light attenuation relates to the turbidity of a formulation. Turbidity is produced by aggregation or precipitation of proteins or complexes in the formulation. Other methods for assessing physical stability are well-known in the art including visual assessments of presence or absence of particles or by detecting fibril/gel formation by Thioflavin T fluorescence microscopy.

Other embodiments of the invention provide pharmaceutical compositions suitable for administration to a patient, particularly to a human being, comprising a therapeutically effective amount of at least one PEGylated insulin lispro compound of Formula I and one or more pharmaceutically acceptable excipients, diluents, buffers, metal ions, or carriers. Such pharmaceutical compositions are typically, though not necessarily, parenteral in nature and may be prepared by any of a variety of techniques using conventional excipients, buffers, diluents, metal ions, or carriers for parenteral products which are well known in the art.

Because the PEGylated insulin lispro compounds of the present invention are very water-soluble, a pharmaceutical composition of the present invention includes a composition comprising water as the primary solvent, PEGylated insulin lispro compounds at a total concentration of at least 1 mg/mL, at least 2 mg/mL, at least 5 mg/mL, at least 10 mg/mL, at least 15 mg/mL, at least 20 mg/mL, at least 25 mg/mL, at least 30 mg/mL, at least 35 mg/mL, at least 40 mg/mL, at least 45 mg/mL, at least 50 mg/mL, or greater and a pharmaceutically acceptable buffer wherein the pharmaceutical composition has a pH from about 4.0 to about 8.5. Preferably, a pharmaceutical composition of the present invention has a pH between about 6.0 and about 8.5. More preferably, a pharmaceutical composition of the invention comprises PEGylated insulin lispro compounds at a total concentration in the range from about 2.5 mg/mL to about 60 mg/mL and a buffer wherein the composition has a pH in the range from about 6.0 to about 8.5. More preferably, a pharmaceutical composition of the invention comprises PEGylated insulin lispro compounds at a concentration in the range from about 5 mg/mL to about 50 mg/mL and a buffer wherein the pharmaceutical composition has a pH in the range from about 6.5 to about 7.5. Even more preferably, a pharmaceutical composition of the invention comprises PEGylated insulin lispro compounds at a concentration in the range from about 10 mg/mL to about 40 mg/mL and a buffer wherein the pharmaceutical composition has a pH in the range from about 6.5 to about 7.5. Even more preferably, a pharmaceutical composition of the invention comprises PEGylated insulin lispro compounds at a concentration in the range from about 15 mg/mL to about 40 mg/mL and a buffer wherein the pharmaceutical composition has a pH in the range from about 7.0 to about 7.5, or from about 7.0 to about 8.0. Even more preferably, a pharmaceutical composition of the invention further comprises a therapeutically effective amount of an insulin. Even more preferably, the insulin is an insulin analog. Even more preferably, the insulin analog is a rapid-acting insulin analog. Most preferably, the rapid-acting insulin analog is insulin lispro.

The term "buffer" refers to a solution that resists changes in pH by the action of its acid-base conjugate components. Preferably, the buffers employed are pharmaceutically acceptable buffers. The phrase "pharmaceutically acceptable buffer" refers to a solution that is safe for use in insulin formulations and that has the effect of controlling the pH of the pharmaceutical composition at the pH desired. In preferred embodiments, the buffer has a pH in the range from about 6.0 to about 8.5. More preferably, the buffer has a pH in the range from about 7.0 to about 8.0. Pharmaceutically acceptable buffers for controlling pH of the compositions of the present invention in this range include, but are not limited to, agents such as phosphate, acetate, citrate, arginine, TRIS, and histidine buffers, as well as combinations thereof. "TRIS" refers to 2-amino-2-hydroxymethyl-1,3,-propanediol, and to any pharmacologically acceptable salt thereof. The free base and the hydrochloride form (i.e., TRIS-HCl) are two common forms of TRIS. TRIS is also known in the art as trimethylol aminomethane, tromethamine, and tris (hydroxy-methyl)aminomethane. Preferably, a pharmaceutical composition of the present invention comprises from about 2.5 mM to about 50 mM phosphate or TRIS buffer. More preferably, a pharmaceutical compositions of the present invention comprises from about 5 mM to about 20 mM phosphate or TRIS buffer. Even more preferably, a pharmaceutical composition of the present invention comprises from about 5 mM to about 10 mM phosphate buffer. Even more preferably, a pharmaceutical composition of the present invention comprises about 5 mM phosphate buffer. Even more preferably, a pharmaceutical composition of the present invention comprises between about 7.5 mM and about 50 mM TRIS buffer. Even more preferably, a pharmaceutical composition of the present invention comprises between about 10 mM and about 25 mM TRIS buffer. Even more preferably, a pharmaceutical composition of the present invention comprises between about 15 mM and about 20 mM TRIS buffer. Most preferably, a pharmaceutical composition of the present invention comprises about 16 mM TRIS buffer.

The PEGylated insulin lispro compounds and compositions of the invention may be formulated analogously with known formulations of insulins that are administered to patients parenterally. Such formulations are known to one skilled in the art. Preferably, PEGylated insulin lispro compounds of Formula I are formulated analogously with the formulation of HUMALOG® insulin lispro or Humulin®. Therefore, a preferred pharmaceutical composition of the present invention may comprise water, a PEGylated insulin lispro compound of Formula I, an isotonicity agent, and a pharmaceutically acceptable buffer. Preferably, a pharmaceutical composition of the invention further comprises a pharmaceutically-acceptable preservative. More preferably, a pharmaceutical composition of the invention further comprises a divalent cation such as zinc and/or cobalt, which can faciliate hexamerization of insulin. Even more preferably, a pharmaceutical composition of the invention further comprises at least one hexamer-stabilizing agent. Furthermore, hydrochloric acid and/or sodium hydroxide may be added to adjust pH.

An "isotonicity agent" is a compound that is physiologically tolerated and imparts a suitable tonicity to a formulation to prevent the net flow of water across cell membranes that are in contact with an administered pharmaceutical composition. Glycerol, which is also known as glycerin, is commonly used as an isotonicity agent. Other isotonicity agents include i) other sugar alcohols such as but not limited to mannitol and sorbitol, ii) salts such as, but not limited to, NaCl, iii) monosaccharides including, but not limited to, dextrose, and iv) disaccharides including, but not limited to, lactose, sucrose, and trehalose. The pharmaceutical compositions of the present invention may include one or more isotonicity agents. Preferably, pharmaceutical formulations of the present invention have one or more isotonicity agents which produce a formulation with an isotonicity in the range of about 270 and about 330 mOsm. More preferably, the isotonicity agent(s) is glycerol, sorbitol, sucrose, NaCl, trehalose, and/or mannitol. Even more preferably, the isotonicity agent is glycerol, sorbitol, sucrose, NaCl, and/or trehalose. Even more preferably, glycerol, sorbitol, sucrose, NaCl, or trehalose at a concentration from about 100 to about 200 mM is present in the pharmaceutical compositions of the present invention. Even more preferably, glycerol at a concentration from about 100 to about 200 mM is present in the pharmaceutical compositions of the present invention. Even more preferably, glycerol at a concentration from about 150 to about 180 mM is present in the pharmaceutical compositions of the present invention. Even more preferably, glycerol at a concentration from about 130 to about 175 mM is present in the pharmaceutical compositions of the present invention. Even more preferably, NaCl at a concentration from about 50 to about 300 mM is present in the pharmaceutical compositions of the present invention. Even more preferably, NaCl at a concentration from about 100 to about 200 mM is present in the pharmaceutical compositions of the present invention. Most preferably, NaCl at a concentration of about 150 mM is present in the pharmaceutical compositions of the present invention.

The pharmaceutical compositions of the present invention may also contain a hexamer-stabilizing compound. The phrases "hexamer-stabilizing compound" refers to a non-proteinaceous, small molecular weight compound that stabilizes the PEGylated insulin lispro compounds of the present invention in a hexameric association state. Calcium ions, zinc, cobalt, copper, nickel, iron, magnesium, manganese, anions, particularly, chloride, bromide, iodide, thiocyanate, and phenolic compounds, particularly phenol, phenolic preservatives, resorcinol, 4'-hydroxyacetanilide, 4-hydroxybenzamide, and 2,7-dihyroxynaphthalene, are known hexamer-stabilizing compounds for insulin molecules. Preferably, the hexamer-stabilizing compound is phenol, m-cresol, o-cresol, p-cresol, chlorocresol, methylparaben, calcium, chloride, or a combination of two or more of these compounds. More preferably, the hexamer-stabilizing compound is phenol, m-cresol, calcium, chloride, or a combination thereof. Preferably, a pharmaceutical composition of the invention comprises between about 1 mM and 75 mM calcium, between about 1 mM and about 50 mM calcium, between about 1 mM and about 25 mM calcium, between about 5 mM and about 50 mM calcium, between about 2.5 mM and about 30 mM calcium, between about 2.5 mM and about 15 mM calcium, between about 2.5 mM and about 10 mM calcium, between about 5 mM and about 30 mM calcium, between about 5 mM and about 15 mM calcium. More preferably, a pharmaceutical composition of the invention comprises between about 2.5 mM and 10 mM calcium.

Multi-use formulations of the pharmaceutical compositions of the present invention may also contain a preservative. The term "preservative" refers to a compound added to a pharmaceutical formulation to act as an anti-microbial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. Certain phenolic preservatives, such as methylparaben, phenol, and m-cresol, are known to bind to insulin and insulin-like molecules and thereby to induce conformational changes that increase either physical or chemical stability, or both (See, e.g., Birnbaum, D. T., et al., *Pharmaceutical. Res.* 14:25-36 (1997); Rahuel-Clermont, S., et al., *Biochemistry* 36:5837-5845 (1997)). "Phenolic preservative" includes the compounds phenol, m-cresol, o-cresol, p-cresol, chlorocresol, methylparaben, and mixtures thereof. The preservative used in formulations of the PEGylated insulin lispro compounds of the present invention may be a phenolic preservative, and may be the same as, or different from the hexamer-stabilizing compound. Preferably, the phenolic preservative is m-cresol or phenol. More preferably, a pharmaceutical compositions of the present invention comprises phenol and/or m-cresol at a concentration from about 0.1 to about 75 mM as a preservative at a pH from about 7.0 to about pH 8.0. Even more preferably, a pharmaceutical composition of the present invention comprises phenol and/or m-cresol at a concentration from about 1 to about 60 mM as a preservative at a pH from about 7.0 to about pH 8.0. Even more preferably, a pharmaceutical composition of the present invention comprises phenol and/or m-cresol at a concentration from about 10 to about 40 mM as a preservative at a pH from about 7.0 to about pH 8.0. Even more preferably, a pharmaceutical composition of the present invention comprises phenol and/or m-cresol at a concentration of about 30 mM at a pH from about 7.0 to about pH 8.0. Most preferably, a pharmaceutical composition of the present invention comprises phenol and/or m-cresol at a concentration of about 30 mM at a pH from about 7.3 to about pH 7.5.

As mentioned above, the pharmaceutical compositions of the present invention may comprise divalent metal cations such as zinc or cobalt that drive hexamerization of insulin or otherwise stabilize insulin compounds. "Divalent metal cation" means the ion or ions that participate to form a complex with a multiplicity of protein molecules. The transition metals, the alkaline metals, and the alkaline earth metals are examples of metals that are known to form complexes with insulin compounds. The transitional metals are preferred. Preferably, the divalent metal cation is one or more of the cations selected from the group consisting of zinc, copper, cobalt, nickel, manganese, magnesium, cadmium, and iron. More preferably, zinc is the divalent metal cation. Zinc is known to facilitate the formation of hexamers of insulin and of various insulin analogs and/or derivatives, including insulin lispro. The primary role of divalent cations such as zinc or cobalt in pharmaceutical compositions of the present invention is to facilitate formation of hexamers of the PEGylated insulin lispro compounds of the present invention and/or any other insulins or insulin analogs in a pharmaceutical composition comprising a PEGylated insulin lispro compound of the present invention. In the presence of a phenolic preservative, hexamer formation may be facilitated by bringing the pH of a solution comprising pharmaceutical compositions of the present invention into the neutral region in the presence of Zn(II) ions, or by adding Zn(II) after the pH has been adjusted to the neutral region. Preferably, the ratio of zinc to insulin compound, insulin analog, and/or PEGylated insulin lispro compound is bounded at the lower limit by about 0.33, that is, two zinc atoms per insulin hexamer, insulin analog hexamer and/or PEGylated insulin lispro hexamer. More preferably, the ratio of zinc to insulin compound, insulin analog, and/or PEGylated insulin lispro compound is from about 0.33 to about 0.67. Even more zinc may be used during the process if a compound that competes with the protein for zinc binding, such as citrate or phosphate, is present. Excess zinc above the amount needed for hexamerization may be desirable to more strongly drive hexamerization, e.g., a ratio of zinc to insulin compound, insulin analog, and/or PEGylated insulin lispro compound from about 0.33 to about 0.83. Also, excess zinc above the amount needed for hexamerization can be present in a pharmaceutical composition of the present invention, and may be desirable to improve chemical and physical stability, to improve "suspendability", and possibly to extend time-action further. On the other hand, excessive amounts of zinc in citrate or phosphate buffers might lead to precipitation of zinc citrate or zinc phosphate, respectively, as well as insulin.

In accordance with the present invention, zinc may be present in the formulation in an amount from about 0.3 mole to about 3 moles per mole of insulin, insulin analog, and PEGylated insulin lispro hexamer. More preferably, zinc is present in the pharmaceutical compositions of the present invention in an amount from about 0.3 mole to about 1 mole per mole of total insulin, insulin analog, and PEGylated insulin lispro hexamer. Even more preferably, zinc is present in the pharmaceutical compositions of the present invention in an amount from about 0.3 mole to about 0.7 mole per mole of total insulin, insulin analog, and PEGylated insulin lispro hexamer. Most preferably, zinc is present in the pharmaceutical compositions of the present invention in an amount from about 0.3 mole to about 0.55 mole per mole of insulin, insulin analog, and PEGylated insulin lispro hexamer. The zinc compound that provides zinc for the present invention may be any pharmaceutically acceptable zinc compound. The addition of zinc to insulin preparations is known in the art, as are pharmaceutically acceptable sources of zinc. Preferably, zinc is provided as a salt, such as zinc sulfate, zinc chloride, zinc acetate, zinc citrate, zinc oxide, or zinc nitrate.

In a further embodiment of the invention the pharmaceutical composition of the present invention further comprises one or more surfactants. The term "surfactant" as used herein, includes agents that reduce the surface tension of a liquid by adsorption at the air-liquid interface. Examples of surfactants include, without limitation, nonionic surfactants, such as polysorbates (e.g., polysorbate 80 or polysorbate 20); poloxamers (e.g., poloxamer 188); Triton™ (e.g., Triton™ X-100); polyethyl glycol; polypropyl glycol; and copolymers of ethylene and propylene glycol (e.g., pluronics, PF68). For example, the surfactant can be present in a pharmaceutical composition of the present invention in an amount from about 0.001-0.5%, e.g., from about 0.05-0.3%. Preferably, the surfactant used in the pharmaceutical composition of the present invention is poloxamer 188. More preferably, the surfactant is poloxamer 188 at a concentration between about 0.5 and about 10 mg/mL, between about 1 and about 10 mg/mL, between about 2 and about 10 mg/mL, between about 3 and about 10 mg/mL, between about 4 and about 10 mg/mL, between about 1 and about 5 mg/mL, between about 2 and about 5 mg/mL, between about 3 and about 5 mg/mL, and between about 4 and about 5 mg/mL.

The invention also provides a PEGylated insulin lispro compound of Formula I or a pharmaceutically acceptable salt thereof for use in the treatment of hypoglycemia and/or diabetes, preferably, in humans.

The invention also provides a PEGylated insulin lispro compound of Formula I or a pharmaceutically acceptable salt thereof for use in the manufacture of a medicament for the treatment of hypoglycemia and/or diabetes, preferably, in humans.

Pharmaceutical compositions comprising a PEGylated insulin lispro according to the present invention may be administered parenterally to patients in need of such a treatment. Parenteral administration may be performed by subcutaneous, intramuscular or intravenous injection by means of a syringe, optionally a pen-like syringe, or mechanical driven injector. Alternatively, parenteral administration can be performed by means of an infusion pump.

Preparation 1

GlyA1-HSCH$_2$CH$_2$CO-Insulin Lispro (3) and LysB28-HSCH$_2$CH$_2$CO-Insulin Lispro (4)

One mmol each of Trt-SCH$_2$CH$_2$CO—OH, N-hydroxysuccinimide (NHS), and diisopropylcarbodiimide (DIC) is mixed in 2 mL DMF for 30 minutes to prepare Trt-SCH$_2$CH$_2$CO—NHS ester. One-tenth mmol of insulin lispro is dissolved in 10 mL of 5% triethylamine (TEA) in DMSO. To the solution is added 0.2 mmol activated Trt-SCH$_2$CH$_2$CO—NHS. After 2 hours at room temperature, 0.2 mL ethanolamine is added to terminate the reaction. The reaction mixture is then diluted with 90 mL of H$_2$O and applied onto a RP-C18 column for purification. The desired fractions of LysB28-Trt-SCH$_2$CH$_2$CO-insulin lispro (2) are pooled and lyophilized. Separately, the desired fractions of GlyA1-Trt-SCH$_2$CH$_2$CO-insulin lispro (1) are pooled and lyophilized. One-tenth mmol of (1) or (2) is dissolved in 5 mL TFA containing 0.2 mL of thioanisole and 0.4 mL of triisopropyl-silane. After 30 min, TFA is removed by evaporation and the residual peptide is taken in 50 mL of 10% ACN in H$_2$O. The resulting solution is applied to a RP-C18 column for purification. The desired fractions of (3) or (4) are pooled and, optionally, lyophilized.

Preparation 2

PheB1-HSCH$_2$CH$_2$CO-insulin lispro (7)

One-tenth mmol of insulin lispro is dissolved in 10 mL of 5% TEA in DMSO. To the solution is added 0.2 mmol of di-tert-butylcarbonate in DMSO. After 1 hour at room temperature, 0.2 mL ethanolamine is added to terminate the reaction. The reaction mixture is then diluted with 90 mL of H$_2$O and applied onto a RP-C18 column for purification. The desired fractions of Boc-GlyA1, Boc-LysB28-insulin lispro are pooled and lyophilized to yield (5). One-tenth mmol of (5) is dissolved in 10 mL of 5% TEA in DMSO. To the solution is added 0.2 mmol activated Trt-SCH$_2$CH$_2$CO—NHS. After 2 hours at room temperature, 0.2 mL ethanolamine is added to terminate the reaction. The reaction mixture is then diluted with 90 mL of H$_2$O and applied onto a RP-C18 column for purification. The desired fractions are pooled and lyophilized to yield Trt-SCH$_2$CH$_2$CO-PheB1, Boc-GlyA1, Boc-LysB28-insulin lispro (6). One-tenth mmol of (6) is dissolved in 5 mL TFA containing 0.2 mL of thioanisole and 0.4 mL of triisopropylsilane. After 30 min, TFA is removed by evaporation and the residual peptide is taken in 50 mL of 10% ACN in H₂O. The resulting solution is applied to a RP-C18 column for purification. The desired fractions are pooled and lyophilized to yield (7).

Example 1

PEGylation of Thiol-Derivatized Insulin Lispro Intermediates

Monomethoxy-PEG-MAL having an average molecular weight of about 20 kDa (b), 30 kDa (a), 40 kDa (a), or 60 kDa (c) is dissolved in a 1:1 mixture of 100 mM NH₄Ac buffer (pH 4.69) and ACN. A lyophilized powder of a thiol-derivatized insulin lispro, e.g., compound (3), (4), or (7), is added to the solution. The reaction may be followed by analytical RP-HPLC. When the reaction is complete (usually after approximately 4 hours), the mixture is diluted with H₂O and applied onto a RP-HPLC column for purification. The desired fractions are pooled and lyophilized to yield the PEGylated insulin lispro compounds. Exemplary PEGylated insulin lispro compounds prepared as described in Example 1 are shown below as (8(a)), (8(b)), (9(a)), (9(b)), (10(a)), (10(b)), and (15(c)). Preferably, these PEGylated insulin lispro compounds will have n in the range from about 400 to about 1000. More preferably, these PEGylated insulin lispro compounds will have n in the range from about 400 to about 750. More preferably, these PEGylated insulin lispro compounds will have n in the range from about 400 to about 550. Even more preferably, these PEGylated insulin lispro compounds will have n of about 400 and about 500. Even more preferably, these PEGylated insulin lispro compounds will have n of about 450 and about 500. Most preferably, these PEGylated insulin lispro compounds will have n of about 450.

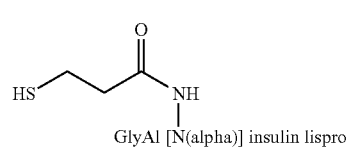

(3)

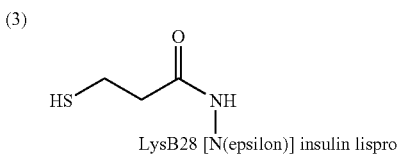

(4)

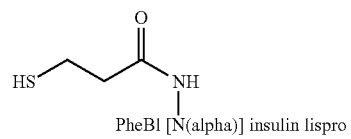

(7)

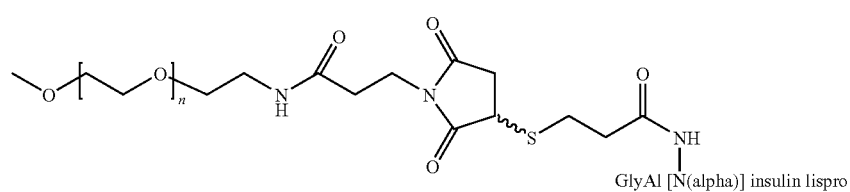

(8(a))

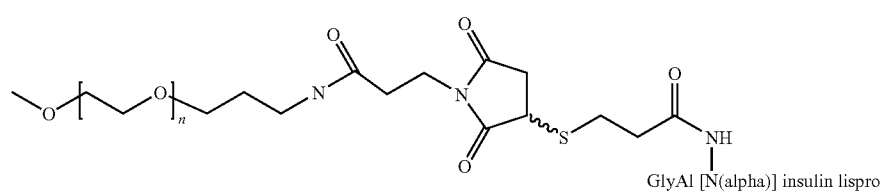

(8(b))

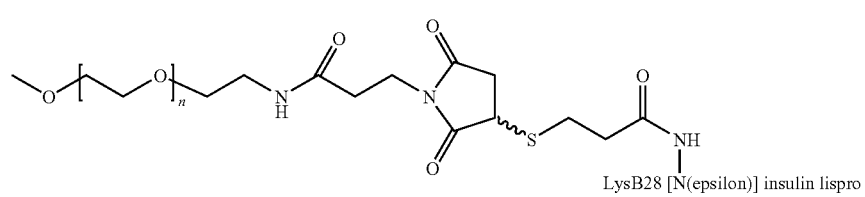

(9(a))

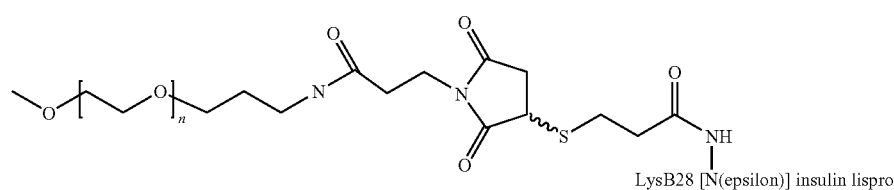

(9(b))

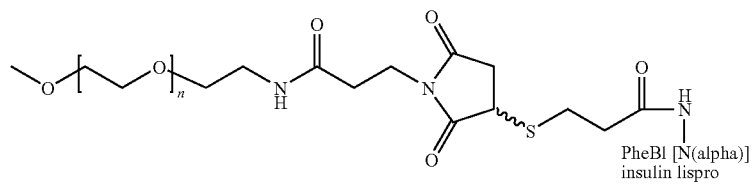

PheB1 [N(alpha)] insulin lispro (10(a))

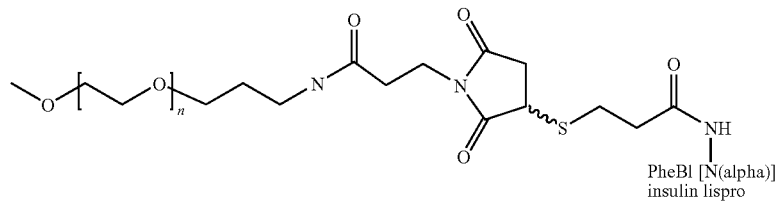

PheB1 [N(alpha)] insulin lispro (10(b))

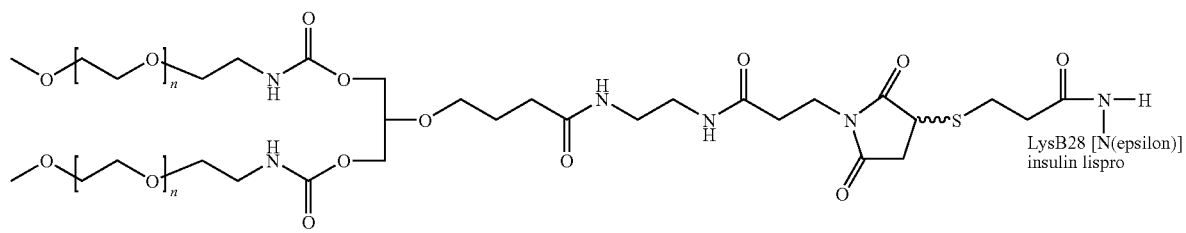

LysB28 [N(epsilon)] insulin lispro (15(c))

Example 2

PEGylation of Insulin Lispro Using Monomethoxypoly(Ethylene Glycol) p-Nitrophenyl Carbonate (mPEG-NPC)

One-tenth mmol insulin lispro is dissolved in 20 mL of 0.2 M borate buffer, pH 10.5, and 1.98 g mPEG-NPC having an average molecular weight of about 20 kDa in 20 mL ACN is added to the solution with vigorous stirring. The reaction is monitored by RP-HPLC and SEC. After approximately 4 hours, the reaction mixture is acidified to pH 5-7 using acetic acid and applied onto a RP-HPLC column for purification. The desired fractions are pooled and lyophilized to yield mono-PEGylated PEG20K-insulin lispro in a yield ranging from 20 to 45%. The identity and purity are confirmed by RP-HPLC, SEC, and MALDI-MS. The ratio of mPEG attached onto A-chain or B-chain is determined by the area integrations of free A-chain and B-chain released after the treatment of the resulting conjugate with tris(2-carboxyethyl) phosphine hydrochloride (TCEP). The ratio of mPEG-NPC to insulin lispro determines the product distribution of mono-PEGylated and di-PEGylated species. The reaction pH governs the site-specificity of PEGylation. As pH increases from about 8 to about 12, compound (11) becomes the major product. When the reaction is conducted at pH 10.5 with mPEG-NPC having an average molecular weight of about 20 kDa (n is about 450), the ratio of (11) to (12) is about 85:15.

The PEGylation reaction described above can also be conducted in a non-buffered aqueous solution by maintaining the pH of the reaction mixture by continuous addition of 0.2 M NaOH. When conducted in a non-buffered aqueous solution using mPEG-NPC having an average molecular weight of about 20 kDa while the pH is maintained at about pH 11.5, the PEGylation reaction products include (11) and (12) in a ratio of about 92:8. Preferably, compound (11) will have n in the range from about 400 to about 1000. More preferably, compound (11) will have n in the range from about 400 to about 750. Even more preferably, compound (11) will have n in the range from about 400 to about 550. Even more preferably, compound (11) will have n of about 400 to about 500. Even more preferably, compound (11) will have n of about 450 and about 500. Most preferably, compound (11) will have n of about 450.

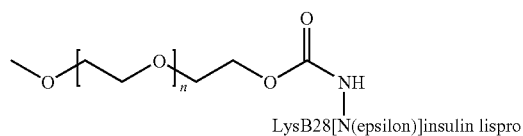

LysB28[N(epsilon)]insulin lispro (11)

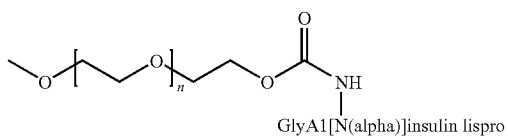

GlyA1[N(alpha)]insulin lispro (12)

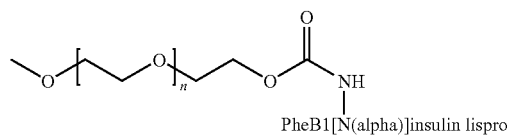

PheB1[N(alpha)]insulin lispro (13)

(14)

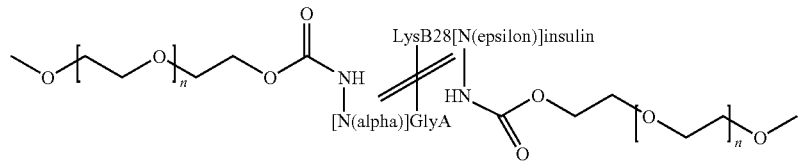

Example 3

In Vitro Receptor Affinity

Receptor binding assays are performed on PI membranes prepared from stably transfected 293 EBNA HEK cells over-expressing the human insulin receptor (hIR) or human IGF-1 receptor (hIGF-1R). Binding affinities are determined from a competitive radio-ligand binding assay using either human recombinant (3-[$^{125}$I]iodotyrosyl A$^{14}$)-Insulin (2000 Ci/mmol) or human recombinant [$^{125}$I]Insulin Like Growth Factor 1 (2000 Ci/mmol). The assay was performed with a SPA method using PVT PEI-treated Type A wheat germ agglutinin-coupled SPA beads. SPA assay buffer (50 mM TRIS-HCl, pH 7.5, 150 mM NaCl, 0.1% BSA) was used for all reagent preparations. Three-fold serial dilutions of compounds (100 nM to 2 pM) are prepared in assay buffer using a Freedom/Evo robot (Tecan) and added to 96-well white, clear-bottom microplates (Corning/Costar) with a Multimek (Beckman Coulter). Radioligand, membranes and SPA beads are added using a multidrop instrument (Titertek). Following a 10-hour incubation at room temperature, the radioactivity is determined using a Microbeta Trilux scintillation counter. Unlabeled insulin lispro and unlabeled IGF-1 are included in each experiment as positive and negative controls, respectively. IC$_{50}$ values are determined from 4-parameter logistic non-linear regression analysis. The affinity constant (Ki) is calculated from the IC50 value based upon the equation Ki=IC50/(1+D/Kd) where D equals the concentration of radioligand used in the experiment and Kd equals the equilibrium binding affinity constant of the radioligand determined from saturation binding analysis (Kd for hIR and hIGF-1R is 0.124 and 0.130 nM, respectively). The geometric mean Ki reported below is 10^(Mean Log Ki) wherein Mean Log Ki=Average (Ki1+Ki2+Ki3 ... Kin) and the number of independent experiments (n) is greater than two. However, where noted below with respect to human IGF-1, n is two.

The following PEGylated insulin lispro compounds prepared as described in Example 1 have a geometric mean Ki less than 30 nM in the hIR binding assay described above: compound 10(a) prepared using linear mPEG-MAL having an average molecular weight of about 40 kDa, compound 8(a) prepared using linear mPEG-MAL having an average molecular weight of about 40 kDa, compound 15(c) prepared using bifurcated mPEG-MAL having an average molecular weight of about 60 kDa, compound 9(a) prepared using linear mPEG-MAL having an average molecular weight of about 30 kDa, compound 9(a) prepared using linear mPEG-MAL having an average molecular weight of about 40 kDa, and compound 9(b) prepared using linear mPEG-MAL having an average molecule weight of 20 kDa. In the hIR and hIGFR binding assays, compound 9(a) prepared using linear mPEG-MAL having an average molecular weight of about 40 kDa has a geometric mean Ki of 3.07 nM±0.32 nM (±S.E.M; n=6) and greater than 84.3 nM (SEM=not determined; n=6), respectively. Additionally, heterogenous PEGylated insulin lispro products generated as described in Example 2 using a linear mPEG-NPC of either 40, 30, or 20 kDa also have a geometric mean Ki less than 30 nM in the hIR binding assay described above. In the hIR binding assay described above, insulin lispro has a geometric mean Ki of 0.22±0.072 nM (±SEM; n=4). In the hIGFR binding assay described above, all of the aforementioned compounds have a geometric mean Ki greater than 75 nM and human IGF-1 has a geometric mean Ki of 1.51±0.23 nM (±SEM; n=2).

These data show that PEGylating position B28 reduces hIR affinity by about 10-fold, making these PEGylated species of insulin lispro weak agonists of the hIR. The PEGylated insulin lispro species also possess no measurable IGFR-1 binding properties in this assay under these conditions.

Example 4

Evaluation of the Potency of PEGylated Insulin Lispro Using an Insulin Receptor Phosphorylation Whole Cell Assay The PEGylated insulin lispro compounds of the present invention may be evaluated for functional activity using DELFIA®, a heterogeneous time-resolved fluorometric assay method available commercially (Perkin-Elmer). Briefly, 293HEK cells over-expressing the human insulin receptor are trypsinized and plated at 60,000 cells/well in poly-D-lysine-coated, half-area Costar 96-well tissue culture plates in serum-free media (SFM), (DMEM with 0.1% fatty acid-free BSA). The cell culture plates are incubated overnight at 37° C. in a CO$_2$ incubator. Anti-insulin receptor A-chain mAb 8314 capture plates are also prepared the night before using Costar ½ area black 96-well microtiter plate, treated overnight at 4° C. with 30 µL of anti-insulin receptor A-chain mAb 8314 (Soos, M. A., et al. *Biochem J* 235:199-208 (1986); available commercially including from Abcam, Inc., Cambridge, Mass.), diluted to 1 µg/mL in 10 mM sodium carbonate. The mAb 8314 capture plates are washed four times with 50 mM TRIS, pH 7.5, 150 mM NaCl, and 0.1% Tween (TBST) to remove any unbound mAb 8314. The mAb 8314 capture plate is then blocked for more than 1 hour at 4° C. with 1% BSA in TBST. After blocking, the capture plate is washed twice with TBST to remove excess BSA solution. Once the capture plate is in the blocking buffer, the cell culture plates are removed from the incubator and equilibrated to room temperature. The test compounds are serially diluted into SFM. To stimulate autophosphorylation of the insulin receptor, 50 µL of the diluted testing agent is added to the cell monolayer. After 30 minutes at room temperature, the reaction is stopped by aspirating off the test compounds and adding back 50 µL of a 2× lysis buffer (2% NP40, 100 mM TRIS, pH 7.4, 300 mM NaCl, Roche Complete™ protease inhibitors with EDTA, and 4 mM vanadate). After 30 minutes in lysis buffer at room temperature, 30 µL of lysate is transferred to the blocked capture plate containing 30 µL of a Europium-N1-anti-phosphotyrosine PY20-antibody, Eu-N1-PY20 (Perkin Elmer), diluted to 50 ng/mL in 10 mM Hepes, 140 mM NaCl and 0.1% Tween. This mixture is incubated for 1 hour at room temperature followed by 6 washes with TBST to remove unbound Eu-N1-PY20 and cell lysate. Following incubation with 50 μL of Enhancement Solution (Perkin Elmer) for 10 minutes with intermittent shaking as the signal is developed. The phosphorylated insulin receptor is quantitated using a Wallac Victor using Time Resolve Fluorescence Europium settings. Phosphorylation level is calculated as a % of the response for a maximally stimulating dose of insulin (100 nM). The potencies of the insulin analogs are calculated as the EC50 dose using a four parameter fit of the dose response. PEGylated insulin lispro compounds prepared as described in Example 1 having an EC50 of less than 15 nM in the assay described in Example 4 include 10(a) prepared using a linear mPEG-MAL having an average molecular weight of about 40 kDa, 9(a) prepared using a linear mPEG-MAL having an average molecular weight of about 40 kDa, 9(a) prepared using a linear mPEG-MAL having an average molecular weight of about 30 kDa, and 9(b) prepared using a linear mPEG-MAL having an average molecular weight of about 20 kDa. In the assay described in Example 4, compound 9(a) prepared using linear mPEG-MAL has an EC50 of 10.88 nM. Heterogenous PEGylated insulin lispro products generated as described in Example 2 using a linear mPEG-NPC having an average molecular weight of about 40, about 30, or about 20 kDa also have an EC50 of less than 15 nM in the assay described in Example 4. A 50:50 and a 70:30 mixture of compound 8(a) prepared using a linear mPEG-MAL having an average molecular weight of about 40 kDa and compound 9(a) prepared using a linear mPEG-MAL having an average molecular weight of about 40 kDa also have an EC50 of less than 15 nM in the assay described in Example 4. In the same assay, human insulin and insulin lispro have an EC50 of 2.3 and 0.7 nM, respectively.

The data show that PEGylating position B28 reduces hIR in vitro activity by about 10- to 20-fold, making these PEGylated insulin lispro species weak agonists of hIR. The PEGylated insulin lispro species also possess no measurable IGFR-1 binding properties.

Example 5

Evaluation of In Vivo Potency and Pharmacokinetic Profiles of PEGylated Insulin Lispro in a Rat Model of Type 1 Diabetes Ten-week old male Harlan Sprague-Dawley rats (Harlan, Ind.) 250-280 g body weight, are dosed intravenously into their tail vein with 45 mg/kg streptozocotin (STZ) in 0.5 M Citric Acid, pH 4.5, three days prior to study start. At the start of the study animals are sorted into groups based on body weight and blood glucose. Only animals with blood glucose between 400-550 mg/dL are included in the study. In the morning of study start animals receive a single subcutaneous injection of the test compound at one of several pre-determined doses. Periodically, duplicate blood samples are drawn from the tail vein and collected into tubes containing disodium EDTA. Blood glucose levels are measured with a glucometer. Also, plasma is collected from the vein blood sampling and a commercially available rat insulin radioimmunoassay is used to determine the levels of the administered drug in the plasma. The area under the curve for blood glucose over time (mg*h/dL) is calculated for each individual animal and is used for a four-parameter logistic regression to determine the ED50. In this assay, compound 9(a) prepared using a linear mPEG-MAL having an average molecular weight of about 40 kDa, compound 9(a) prepared using a linear mPEG-MAL having an average molecular weight of about 30 kDa, and compound 9(b) prepared using a linear mPEG-MAL having an average molecular weight of about 20 kDa has a potency (ED50) of 241, 138, and 69 nmol/kg, respectively, from a typical dose response curve. Additionally, those compounds were able to lower blood glucose in STZ-treated rats to a level that is normal in this strain of rats (100 mg/dL or below) for at least 36 hours with a single subcutaneous injection of 568 nmol/kg. Insulin detemir on the other hand normalizes glucose for 5-6 hours in the above assay with a 568 nmol/kg single dose.

In addition to assessment of pharmacodynamic parameters, the mean pharmacokinetic parameter values in rats for test compounds are determined using the duplicate blood sample. Pharmacokinetic parameters are calculated using model-independent methods (WinNonlin Pro). The resulting pharmacokinetic parameter values show nonlinearity as function of dose. The range of values reported correspond to pharmacokinetic parameter values generated between the highest dose tested (568 nmol/kg) and the lowest dose (5.6 nmol/kg).

The pharmacokinetic results for compound 9(b) prepared using a linear mPEG-MAL having an average molecular weight of about 20 kDa indicated a time to maximum concentration ($T_{max}$) ranging from 6-12 h, an apparent clearance rate of (CL/F) ranging from 0.05-0.14 L/h/kg, an apparent volume of distribution (V/F) ranging from 0.6-7.2 L/kg, and an elimination half-life ($t_{1/2}$) ranging from 8.5-34.5 h.

The pharmacokinetic results for compound 9(a) prepared using a linear mPEG-MAL having an average molecular weight of about 30 kDa indicated a $T_{max}$ of 12 hours, a CL/F ranging from 0.05-0.13 L/h/kg, a V/F ranging from 0.6-2.0 L/kg, and an $t_{1/2}$ ranging from 8.3-11.0 h.

The pharmacokinetic results for compound 9(a) prepared using a linear mPEG-MAL having an average molecular weight of about 40 kDa indicated a $T_{max}$ ranging from 12-24 h, a CL/F ranging from 0.06-0.2 L/h/kg, a V/F ranging from 1.0-7.5 L/kg, and a $t_{1/2}$ ranging from 11.1-48.5 h.

When insulin lispro is similarly administered to male STZ-treated rats at 568 nmol/kg, a $t_{1/2}$ of about 1 h and a CL/F of about 1.2 L/h/kg is measured.

When insulin detemir is similarly administered to male STZ-treated rats at doses ranging from 18.9-568 nmol/kg, a $t_{1/2}$ of ranging from 1.9-3.1 h and a CL/F of about 0.8-1.7 L/h/kg is observed.

Due to the complexities in the pharmacokinetics, the apparent CL ratios between detemir and exemplary PEGylated insulin lispro compounds are different depending on the dose used for the determination. However, the studies described in Example 5 indicate that exemplary PEGylated insulin lispro compounds conjugated to 20- or 40 kDa PEG have about a 5- to 30-fold slower apparent clearance than detemir in the STZ-induced diabetic rat.

Example 6

Evaluation of In Vivo Duration of Action and Pharmacokinetic Characteristics of PEGylated Insulin Lispro in a Rat Model of Type 2 Diabetes The glucodynamic activity of compound 9(a) with a 40 kDa linear PEG is evaluated in male ZDF fa/fa rats (n=4 rats/group) following a single subcutaneous injection of vehicle control (PBS) or 517 nmol/kg of 9(a) prepared using a linear mPEG-MAL having an average molecular weight of about 40 kDa. Serial samples are collected for both pharmacokinetic and pharmacodynamic characterization. A single subcutaneous administration of 517 nmol/kg of 9(a) prepared using a linear mPEG-MAL having an average molecular weight of about 40 kDa to male ZDF fa/fa rats is associated with statistically significant glucose lowering that is sustained for at least seven days (relative to placebo; p<0.05). Compound 9(a) prepared using a linear mPEG-MAL having an average molecular weight of about 40 kDa exposure is also verifiable over seven days.

Example 7

Phenolic Preservative Titration of PEG-B28$_{(92.4\%)}$ A1$_{(7.6\%)}$-Insulin Lispro, Insulin Lispro, or a Mixture (70% PEG$_{20\ kDa}$-B28$_{(92.4\%)}$A1$_{(7.6\%)}$-Insulin Lispro: 30% insulin lispro) thereof with phenol in the Presence of cobalt Ions PEG$_{20\ kDa}$-B$^{28(92.4\%)}$A1$_{(76\%)}$-insulin lispro or insulin lispro is dissolved in a solution containing 20 mM KSCN and 50 mM TRIS-ClO$_4$ at pH 8.0. The target concentration for either protein is ~4 mg/mL, based on protein content ($\epsilon_{280}$=1.05 (mg/mL)$^{-1}$cm$^{-1}$). Cobalt chloride (41.9 mg) is dissolved with 1 mL of water to yielding a stock solution with a cobalt ion concentration of 0.176 M. An aliquot of the cobalt stock solution (~2 µL depending up on the protein concentration) is added to 0.8 mL protein solution such that the final mole ratio of cobalt ion to insulin hexamer is equal to 4. To assess hexamerization, distortions in the cobalt coordination chemistry were monitored at 574 nm as function of phenolic preservative concentration. Specifically, a concentrated phenol solution (0.564 M) is titrated into 0.8 mL of protein solution using microliter aliquots such that the final volume at the end of the titration does not exceed 0.84 mL. The final solution is stirred for a minimum of 20 minutes after each aliquot of phenol and the visible spectrum of the solution is collected from 400 nm to 800 nm. The absorbance recorded at 574 nm is converted to molar extinction coefficient by dividing the absorbance by the His$^{B10}$-coordinated cobalt molar concentration, i.e., the hexameric protein concentration multiplied by two based on the knowledge that the His$^{B10}$ moieties of insulin hexamers coordinates two divalent metal ions. For the preparation of 70/30 mixtures (mole:mole) formulations of PEG$_{20\ kDa}$-B28$_{(92.4\%)}$/A1$_{(7.6\%)}$-insulin lispro and insulin lispro, the protein is first mixed and then cobalt is added followed by titration with phenolic preservative.

In insulin lispro the natural sequence of proline at position B28 and lysine at position B29 is reversed as compared to wild-type human insulin. This reversal leads to a conformational shift in the C-terminal end of the B chain that sterically hinders the ability of the lispro insulin monomers to form dimers. Thus, the dimer association constant is reduced by a factor of 300 as compared with that of wild-type human insulin. The results, shown in Table I, indicate that PEG$_{20\ kDa}$-B28$_{(92.4\%)}$/A1$_{(7.6\%)}$-insulin lispro can surprisingly and unexpectedly associate as hexameric complex in the presence of divalent metal ions and phenolic preservative analogous to formulation conditions used in Humalog®, in spite of the presence of six 20 kDa PEG moieties conjugated near the already weakened, vis-à-vis wild-type human insulin, dimerization domain of insulin lispro. Moreover, 70/30 mixtures of PEG$_{20\ kDa}$-B28$_{(92.4\%)}$/A1$_{(7.6\%)}$-insulin lispro and insulin lispro also demonstrate the ability to form hexameric complexes, which support the preparation of extemporaneous and/or stable premixed formulations of a basal insulin and rapid-acting insulin.

TABLE I

| Phenol (mM) | $\epsilon_{574\ nm}$ insulin lispro | $\epsilon_{574\ nm}$ PEG$_{20kDa}$-B28$_{(92.4\%)}$/A1$_{(7.6\%)}$-insulin lispro | $\epsilon_{574\ nm}$ 70/30 Mixture |
|---|---|---|---|
| 0.0 | 0 | 0 | 0 |
| 0.1 | 181 | 5 | |
| 0.2 | | | 42 |
| 0.3 | 259 | | 93 |
| 0.4 | 329 | | 125 |
| 0.6 | 347 | 26 | |
| 0.7 | 391 | 45 | 182 |
| 0.9 | 468 | | |
| 1.1 | 514 | 88 | 244 |
| 1.4 | 628 | 146 | |
| 1.8 | 744 | | 399 |
| 2.1 | 765 | 220 | 462 |
| 2.5 | 760 | | |
| 2.8 | 799 | 358 | 535 |
| 3.5 | 826 | 413 | 567 |
| 4.2 | 828 | | 600 |
| 4.9 | | 392 | 614 |
| 5.6 | | | 635 |
| 6.3 | | 500 | |
| 7.0 | 812 | | 656 |
| 7.7 | | 582 | |
| 9.0 | | 596 | |
| 10.4 | | 610 | 676 |
| 11.7 | | 630 | |
| 13.8 | 865 | 648 | |
| 17.1 | | 662 | 707 |
| 20.4 | 886 | 696 | |
| 23.7 | | | 736 |
| 26.9 | 903 | 725 | 764 |

Example 8

Analysis of Hexameric State of PEG$_{20\ kDa}$-B28$_{(92.4\%)}$/A1$_{(7.6\%)}$-Insulin Lispro Formulated with Zn, Phenol, and/or Calcium The chemical shelf-life and in-use stabilities of insulin and some insulin analogs benefit from the ability to form discrete hexameric complexes in solution. The ability to hexamerize insulin or insulin lispro, in the presence of divalent metal ions (Zn$^{+2}$ or Co$^{+2}$) and phenolic preservatives (phenol or m-cresol), slows deamidation of AsnA21 and subsequently minimizes high molecular weight particle (HMWP) formation.

To assess the ability for PEG20 kDa-LysB28-insulin lispro to form hexamers, PEG$_{20\ kDa}$-B28$_{(92.4\%)}$/A1$_{(7.6\%)}$-insulin lispro, with a starting protein concentration based on A$_{276\ nm}$=8.6 mg insulin lispro/mL or 38.2 mg PEGylated insulin lispro conjugate/mL, at pH 6.7 is dialyzed in water overnight. The dialyzed protein is then diluted with water to adjust the protein concentration to 4.6 mg/mL or 20.6 mg of PEGylated protein conjugate/mL. A 4× buffer stock solution is prepared at pH 7.0, with the final the concentrations of the phosphate buffer at 40 mM and m-cresol at 12.8 mg/mL. The zinc oxide stock solution is prepared by dissolving zinc oxide in 0.5 mL of 1 N HCl then diluting with water to a final zinc concentration of 0.097 M. Solution samples for near-UV circular dichroism (CD) analysis are prepared with varying zinc concentrations (0 to 400 µM) by mixing 450 µL of the PEG$_{20\ kDa}$-B28$_{(92.4\%)}$/A1$_{(7.6\%)}$-insulin at a protein concentration of 4.6 mg/mL with aliquots of zinc stock solution (the maximum total volume of zinc stock solution added=2.5 µL or equivalent to 4 zinc ions per PEG$_{20\ kDa}$-B28$_{(92.4\%)}$/A1$_{(7.6\%)}$-insulin hexamer), and 150 µL of the 4× phosphate buffer stock solution. The final pH is adjusted, if necessary to pH~7.0. Hexameric association of the PEG$_{20\ kDa}$-B28$_{(96\%)}$/A1$_{(4\%)}$-insulin lispro or insulin lispro is monitored in the near-UV circular dichroism at 250 nm, a region sensitive to disulfide changes, using a 0.2 cm cell. The mean residue ellipticity is plotted versus a ratio of moles zinc per moles hexamer.

The results, shown in Table II, further indicate that PEG$_{20\ kDa}$-B28$_{(92.4\%)}$/A1$_{(7.6\%)}$-insulin can surprisingly and unexpectedly associate as hexameric complex in the presence of divalent metal ions and phenolic preservative in formulation conditions analogous to those of Humalog®, in spite of the presence of six 20 kDa PEG moieties conjugated near the already weakened, relative to wild-type human insulin, dimerization domain of insulin lispro.

The impact of hexamerization and ligand binding on thermal stability of PEG$_{20\ kDa}$-B28$_{(92.4\%)}$/A1$_{(7.6\%)}$-insulin in hexamer promoting test formulations was also investigated with CD thermal denaturation experiments. The wavelength used for the thermal denaturation studies was 240 nm because it was found the overall signal change was greater at 240 nm than the 250 nm used in the Zn$^{2+}$ binding studies, yet the total solution absorbance would be low enough for high quality CD data to be obtained. Thermal scan data at 240 nm in a 1 mm cuvette were collected from 5° C. to approximately 95° C. (final temperature varied slightly for each sample), with a scan rate and data pitch of 1° C./minute, bandwidth of 1.5 nm, and response time of 8 seconds. Thermal denaturation data may be plotted as both the raw signal (mdeg at 240 nm) and the fraction apparent unfolded (Funf), which is given by: $F_{unf}(T)=[Y_{obs}(T)-Y_{nat}(T)]/[Y_{unf}(T)-Y_{nat}(T)]$ where $Y_{obs}(T)$ is the observed signal as a function of temperature, and $Y_{nat}(T)$ and $Y_{unf}(T)$ are linear extrapolations of the native and unfolded baselines, respectively. The unfolding onset temperature is defined as the temperature at which $F_{unf}$ begins to increase from the native baseline ($F_{unf}=0$), and the midpoint temperature is the temperature at which $F_{unf}=0.5$.

CD thermal denaturation experiments performed essentially as described above indicated that the thermal stability of PEG$_{20\ kDa}$-B28$_{(92.4\%)}$/A1$_{(7.6\%)}$-insulin hexamers is substantially reduced compared to insulin lispro hexamers when both are similarly formulated in 16 mM TRIS, pH 7.2, 3.1 mg/ml m-cresol, and zinc. Furthermore, the CD thermal denaturation studies detected a significant calcium and chloride ion concentration dependent increase in melting temperature for PEG$_{20\ kDa}$-B$^{28}$$_{(92.4\%)}$/A1$_{(7.6\%)}$-insulin lispro (data not shown). More specifically, the onset temperature of unfolding was observed to be ~30° C. in 16 mM TRIS, pH 7.2, 3.1 mg/ml m-cresol, and zinc but increases dramatically to ~50° C. in the same formulation having 75 mM calcium chloride. A similar effect was observed as the r upon the addition of NaCl (25 mM to 150 mM NaCl) rather than calcium chloride to the formulation. Therefore, calcium and/or chloride may be very useful hexamer-promoting excipients in pharmaceutical compositions comprising PEG$_{20\ kDa}$-B28-insulin lispro compounds in order to increase the chemical and/or physical stability of the pharmaceutical composition upon storage.

TABLE II

Mean Residue Ellipticity (MRE) changes as a function Zn/hexamer ratio

| Zn per hexamer (mol/mol) | MRE PEG$_{20\ kDa}$-B28$_{(96\%)}$/A1$_{(4\%)}$-insulin lispro (degrees cm$^2$ dmol$^{-1}$ residue$^{-1}$) | MRE Insulin lispro (degrees cm$^2$ dmol$^{-1}$ residue$^{-1}$) |
| --- | --- | --- |
| 0 | −116.103 | −172.545 |
| 0.5 | −135.764 | −209.347 |
| 1 | −158.861 | −268.082 |
| 1.5 | −190.81 | −315.972 |
| 2 | −213.12 | −378.179 |
| 3 | −255.23 | −426.872 |
| 4 | −298.729 | −471.587 |

Example 9

Generation of PEG$_{20\ kDa}$-B28$_{(~95\%)}$/A1$_{(~5\%)}$-Insulin Lispro

A buffer solution containing 150 mM sodium phosphate dibasic and 50 mM EDTA is mixed with 150 mM sodium phosphate tribasic to yield a buffer solution with a pH between 10.85 and 11.10 at a temperature between about 4 and 6° C. At a temperature between about 4 and 6° C., insulin lispro crystals (30-60 mg/mL) are slowly added to the buffer with gentle agitation to avoid formation of agglomerates during crystal dissolution.

Monomethoxypoly(ethylene glycol) p-nitrophenyl carbonate (mPEG-NPC) having PEG of a weight average molecular weight of about 20 kDa±about 2 kDa is dissolved at a concentration from 60-120 mg/mL in chilled water (4-6° C.) by placing the required amount of chilled water in a vessel, agitating to create a vortex, and slowly pouring the mPEG-NPC powder into the eye of the vortex to ensure adequate and rapid dispersion. mPEG-NPC powder is a fine powder and upon dispersion considerable air bubbles are released into the vessel. The mPEG-NPC solution in the vessel is allowed to de-aerate between 30 to 60 minutes, depending on volume.

The insulin lispro solution prepared above is transferred to a mechanically agitated jacketed vessel. The vessel is instrumented for measurement of temperature and pH. Agitation is provided by a standard impeller operating at a Reynolds number in the turbulent regime. The mPEG-NPC (PEG) solution is metered into the vessel at rate to give a total PEG addition time of between 3 to 5 hours. The temperature of the jacket is maintained between 4° C. and 6° C. and mixing is continued. The pH of the reaction is maintained between 10.85 to 11.10 by the addition of the required amount of the 150 mM sodium phosphate tribasic buffer. The PEG is added until the final PEG:insulin lispro molar ratio is in the range between 2.5 to 4.5.

At the end of the PEG addition, the jacket temperature is raised within 60 minutes to between 25° C. and 30° C. and the reaction mixture is incubated at that temperature for about 3 to about 6 hours while maintaining the pH between about 10.7 to about 11.0. At the end of incubation period, the reaction mixture is quenched by the addition of 2× buffer (100 mM acidic acid/sodium acetate, pH 4.0) and diluted with the same 2× buffer to adjust its conductivity (2.5 mS/cm) and concentration (3-5 mg/mL).

The reaction mixture is purified using a cation exchange chromatography (CEX) column packed with an appropriate resin (e.g., Fast Flow SP Sepharose resin). The column is packed with resin to a bed height between about 15 to about 30 cm, equilibrated with 100 mM Na-Acetate (buffer A) and loaded with the diluted reaction mixture (5-8 gm product/L of resin) at low pH (about 2.5 to about 4.0) at an appropriate flow rate of between about 50 to about 90 cm/h. The mono-PEGylated product and unreacted protein preferentially bind onto the resin while multi-PEGylated by-products and excess reagents mostly pass through the column. Buffer A, with dilute salt concentration (20-30 mM), is used to wash away any weakly adsorbing multi-PEGylated by-products, followed by gradient elution using a buffer (8-12 CV) with increased salt concentration (50-70 mM) to preferentially remove the PEGylated product away from the resin while keeping any unreacted protein onto the column. The product is collected (3-5 CV) and the column is washed with buffer A with high salt concentration (100 mM) to remove un-reacted protein.

The CEX column mainstream (3-5 CV) at 3-5 mg/mL is subjected to a tangential flow filtration to increase its concentration to 40-80 mg/mL using a standard flat sheet membrane (3-5 kDa molecular weight cut-off). The process is carried out via an initial concentration following by buffer exchanges and final concentration to the required concentration. The operating flux throughout the process is maintained between 10-20 liter per meter squared of filter area per hour (LMH) and transmembrane pressure (TMP) between about 15 to about 35 psi.

The final concentrated bulk active pharmaceutical ingredient solution is frozen at an appropriate temperature (−20° C. to −70° C.) and stored at an appropriate temperature (−20° C. to −70° C.).

Example 10

Pharmacokinetic Profiles of PEGylated Insulin Lispro in Dogs

Two-four year old female Beagle dogs, 7-10 kg body weight, are dosed subcutaneously with 18.9 nmol/kg of exemplary test compounds. Periodically, blood samples is drawn from the cephalic or saphenous vein and collected into tubes containing disodium EDTA. Plasma is collected from the vein blood sampling and a commercially available insulin radioimmunoassay was used to determine the levels of the administered drug in the plasma. Pharmacokinetic profiles and parameters were determined for each of the following exemplary compounds prepared essentially as described in Example 2: compound 11 prepared using a linear mPEG-NPC having an average molecular weight of about 40 kDa, about 30 kDa, and about 20 kDa.

Pharmacokinetic parameters were calculated using model-independent methods (WinNonlin Pro). Compound 11 prepared using a linear mPEG-NPC having an average molecular weight of about 20 kDa exhibited a time to maximum concentration ($T_{max}$) of approximately 12 hours, an apparent clearance rate (CL/F) of approximately 0.046 L/h/kg, a maximal concentration ($C_{max}$) of approximately 14 nM, and an elimination half-life ($t_{1/2}$) of approximately 14 hours.

Compound 11 prepared using a linear mPEG-NPC having an average molecular weight of about 30 kDa exhibited a $T_{max}$ of approximately 24 h, a CL/F of approximately 0.027 L/h/kg, a $C_{max}$ of approximately 18 nM, and a $t_{1/2}$ of approximately 23 hours.

Compound 11 prepared using a linear mPEG-NPC having an average molecular weight of about 40 kDa exhibited a $T_{max}$ of approximately 24 h, a CL/F of approximately 0.026 L/h/kg, a $C_{max}$ of approximately 15 nM, and a $t_{1/2}$ of approximately 20 hours.

Insulin detemir was similarly administered to female beagle dogs at a dose of 18.9 nmol/kg, and exhibited a $T_{max}$ of approximately 1.3 hour, a CL/F of approximately 0.12 L/h/kg, a $C_{max}$ of approximately 23 nM, and a $t_{1/2}$ of approximately 3.5 hours. Table III lists the comparable parameters in the dog. The insulin-specific RIA utilized for these studies detects both PEGylated insulin lispro and endogenous insulin.

TABLE III

| | PK parameters for PEGylated insulin lispro in dog | | | |
|---|---|---|---|---|
| Parameter | 20 kDa PEG-compound 11 | 30 kDa PEG-compound 11 | 40 kDa PEG-compound 11 | Insulin detemir |
| $C_{max}$ (nM) | 14 ± 1 | 18 ± 3 | 15 ± 1 | 23 ± 2 |
| $T_{max}$ (hr) | 12 ± 0 | 24 ± 0 | 24 ± 0 | 1.3 ± 0.6 |
| $T_{1/2}$ (hr) | 14 ± 3 | 23 ± 6 | 20 ± 1 | 3.5 ± 0.7 |
| AUC (nM hr) | 419 ± 43 | 727 ± 118 | 729 ± 86 | 161 ± 20 |
| CL/F (L/hr/kg) | 0.046 ± 0.005 | 0.027 ± 0.004 | 0.026 ± 0.003 | 0.12 ± 0.02 |

18.9 nmol/kg Subcutaneous Dose; n=3/Group

Example 11

Projection of Mean 'Flatness' and Dose in Humans

A key criterion for improved basal insulin therapy is the ability to achieve a truly flat profile, amenable to once daily dosing in patients. Sufficient flatness is defined as a peak-trough (PT) ratio of <2. For purposes of comparison, PT ratios calculated from published PK profiles range from ~4-9 for detemir and ~1.2-2.6 for glargine. The rat and dog PK data (see Examples 5 and 10, respectively) for the 18.9 nmol/kg dose of exemplary compounds and insulin detemir were fit to 1-CMT PK models, parameterized in terms of ka, CL/F and V/F. Each PK parameter (P) is then fit to an allometric equation of the form $P=aBW^b$, where b is fixed at −0.25, 0.75 and 1 for ka, CL/F and V/F, respectively, and a is a fitted parameter. Mean human estimates are obtained for each PK parameter, and simulations generated mean profiles following daily dosing in humans. Because of the similarities between the 30 kDa and 40 kDa PEGylated insulin lispro conjugates, the simulations are shown only for 20 kDa PEGylated insulin lispro, 40 kDa PEGylated insulin lispro and insulin detemir. The simulations generated indicate that the peak-trough (PT) ratios for 20 kDa and 40 kDa PEGylated insulin lispro compounds are dramatically flatter than for insulin detemir. Simulations results are shown in FIG. 1.

A strategy for estimating the human dose of a PEGylated insulin lispro required for efficacy is to use a known clinical comparator (insulin detemir) as an internal control in the rat efficacy model, with the assumption that the relative potency between PEGylated insulin lispro and insulin detemir in the rat model is similar to the relative potency in the clinic. The required daily dose of PEGylated insulin lispro in the clinic can be obtained using the following equation:

$$\frac{Dose_{det}}{Dose_{PEG}} = \frac{EC_{50,det}}{EC_{50,PEG}} \times \frac{CL/F_{det}}{CL/F_{PEG}}$$

The relative potency ratio for each of the PEGylated insulin lispro conjugates can be obtained in Table IV. The relative apparent clearance ratios for exemplary PEGylated insulin lispro/detemir in the rat, dog and human (projected) are compiled in Table V.

TABLE IV

Relative concentration-based potency of PEGylated insulin lispro conjugates and insulin detemir in the rat

| Compound 11 | Potency ratio detemir/PEGylated insulin lispro |
|---|---|
| 20 kDa PEG-insulin lispro | 1.34 ± 0.68 |
| 30 kDa PEG-insulin lispro | 0.68 ± 0.35 |
| 40 kDa PEG-insulin lispro | 0.65 ± 0.36 |

TABLE V

Relative CL/F ratios for insulin detemir/PEGylated insulin lispro compounds

| Compound 11 | CL/F Rat | CL/F Dog | CL/F Human (Projected) |
|---|---|---|---|
| 20 kDa PEG-insulin lispro | 5.5 | 2.6 | 3.3 |
| 40 kDa PEG-insulin lispro | 4.8 | 4.6 | 4.1 |

Using the relative potency estimates from Table IV and the relative CL/F estimates from Table V, the mean dose projections for PEGylated insulin lispro conjugates in humans is 4.2 and 6.9 nmol/kg for the 20 kDa and 40 kDa PEGylated insulin lispro compounds, respectively. These projections are based on a mean daily clinical dose of 18.5 nmol/kg insulin detemir as reported for Type 2 diabetic patients in the detemir label. When both time action and potency are considered, the maximum mean clinical dose prediction for is ~3-fold lower than insulin detemir. In the best case, the mean clinical dose estimate for the 20 kDa, 30 kDa, and 40 kDa PEGylated insulin lispro conjugate is about 20- and about 45-fold lower than insulin detemir.

Example 12

Glucose Infusion Rates after Single Administration in Healthy Volunteers: $PEG_{20\ kDa}\text{-}B28_{(\geq\sim95\%)}/A1_{(\leq\sim5\%)}$-insulin lispro and Glargine Administration A three-part first-human-dose study was conducted using a single dose of $PEG_{20\ kDa}\text{-}B^{28}_{(\geq\sim95\%)}/A1_{(\leq\sim5\%)}$-insulin lispro (LY) prepared essentially as described in Example 9. Part A included three study periods, in which subjects received a subcutaneous (SC) injection of LY dose in the first period, followed by an injection of insulin glargine dose (0.5 U/kg) in the second period, and then followed by an injection of another LY dose in the third period. Part B was an open label, single dose, two replicate periods study in which subjects received a single dose of LY in both periods utilizing 24- and 36-hour glucose clamps. Part C was an open label, two period, single dose, fixed sequence, comparator-controlled study in which subjects received a single 0.5 mg/kg SC dose of LY in one period and a single 0.8 U/kg SC dose of insulin glargine in the other period. Subjects underwent a 24-hr glucose clamp procedure in each period in Parts A and C and a longer duration (up to 36-hr) glucose clamp procedure in each period in Part B. LY was administered subcutaneously as a single dose in Parts A, B and C as follows:

Part A doses: 0.0025, 0.0125, 0.075, 0.325 mg/kg body weight
Part B doses: 0.15, 0.225 mg/kg
Part C dose: 0.5 mg/kg Subjects are administered a single dose of the PEGylated insulin lispro compound or a single dose of insulin glargine (0.5 U/kg) as a comparator and another single dose of LY in the $3^{rd}$ period. In all treatment periods, subjects undergo a euglycaemic clamp procedure for up to 24/36 hours following each insulin compound injection. Glucose infusion rates (GIR) are adjusted to maintain euglycaemia, with the documented GIR over time providing the GD measure of insulin action. The aim of the euglycaemic glucose clamp is to maintain euglycaemia through glucose infusion after the administration of a dose of an insulin compound. It is assumed that endogenous insulin secretion and hepatic glucose output are minimal and that any glucose that is translocated out of the glucose space (i.e., glucose metabolized) is the direct consequence of the administered exogenous insulin. The GIR in this case will be the glucodynamic (GD) measure of the insulin action over time. All glucose clamp studies are performed after an overnight fast of approximately 8 hours. On the morning of the study, a small catheter is placed into a vein of one arm, ideally in the ante-cubital fossa, for administration of 20% dextrose solution (buffered to near neutral pH) under the control of a volumetric pump. Another catheter is placed, ideally in the wrist or hand for venous glucose sampling. This area is heated with a warming device to approximately 55-60° C. for sampling arterialized venous blood. Blood samples are obtained at the bedside for immediate determination of whole blood glucose concentrations using an automated glucose oxidase technique. After basal blood sampling and a stabilization period of approximately 30 minutes, each subject receives a dose of insulin compound administered subcutaneously. The start of the subcutaneous injection of an insulin compound is defined as time zero. Following completion of dosing, in conjunction with frequent blood sampling for measurement of blood glucose, glucose is infused intravenously at a variable rate in order to maintain euglycaemia for up to 24 or 36 hours after insulin administration.

Blood sampling occurs approximately every 10 minutes for approximately 30 minutes prior to dosing and continued every 5-10 minutes for the first 2 hours after dosing (with the option to sample as frequently as every 2.5 minutes), and then reduced to 10-30 minute intervals up to the end of clamp.

During the glucose clamp, the glucose infusion rate is adjusted to maintain a pre-determined target blood glucose concentration for the individual subject. Preferably, the target concentration is close to the fasting blood glucose. The aim of the glucose clamp procedure is to maintain the blood glucose concentrations within +5% of the pre-dose target value, which is defined as 5 mg/dL below the mean fasting blood glucose. Thus, blood glucose concentrations are kept constant while the GIR varied. Therefore, the varying glucose infusion rate reflects the activity of the test insulin compound. Blood glucose levels from samplings and infusion rate changes throughout the clamp are documented.

Figure 2:
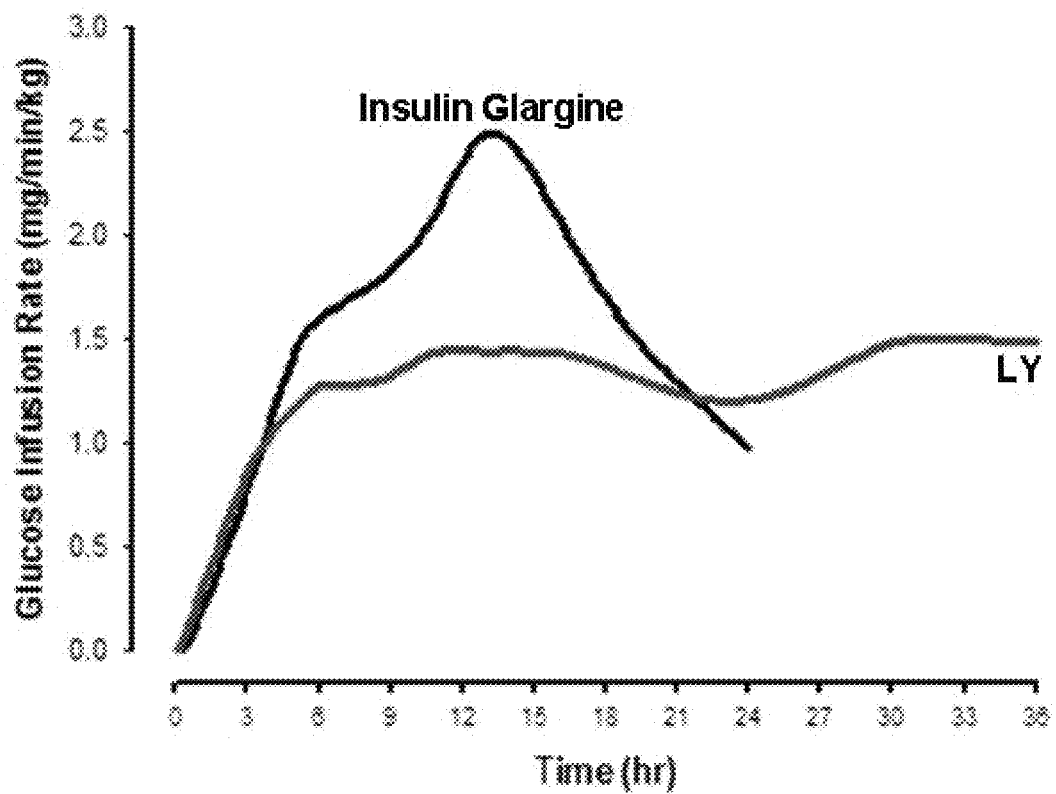
FIG. 2 is a graph of glucose infusion rates (GIR) in humans after a subcutaneous dose of either $PEG_{20\ kDa}$-$B28_{(\geq \sim 95\%)}$/$Al_{(\leq \sim 5\%)}$-insulin lispro (LY; 0.225 mg/kg) or insulin glargine (0.5 U/kg). The GIR profiles are based on observed data and a "loess smooth" (Splus 2000, Professional Edition, MathSoft, Inc) function developed within Lilly Research Laboratories was used to fit the observed data.

A study conducted essentially as described in Example 12 demonstrated, in humans, that LY has features of an ideal "basal" insulin: a long duration of action, an apparent half-life ranging from 24-44 hrs and basal characteristics, i.e., a peak-trough ratio of less than 2 (FIG. 2). Additionally, the duration of action for LY is longer than that of insulin glargine (FIG. 2). The within subject variability in the glucodynamics was less than 30% (data not shown) which is similar to or better than glargine. Finally, glucodynamic data from Part C of the study (0.5 mg/kg) resulted in a GIR profile for LY that was "peakless", maintained GD for greater than 36 hours, and exceeded the peak GIR response for glargine (0.5 U/kg; data not shown).

Example 13

Chemical and Physical Stability of $PEG_{20\ kDa}$-$B28_{(\sim 95\%)}/A1_{(\sim 5\%)}$-insulin lispro Pharmaceutical Compositions As described in Examples 7 and 8 above, $PEG_{20\ kDa}$-$B^{28}_{(\sim 95\%)}/A1_{(\sim 5\%)}$-insulin lispro can associate as a hexameric complex in the presence of divalent metal ions and phenolic preservative in formulation conditions analogous to those of Humalog®. Accordingly, chemical and physical stability studies on $PEG_{20\ kDa}$-B28-insulin lispro formulations similar to commercial solution formulations of insulin lispro (i.e., Humalog® solution formulations) were conducted. Chemical stability of a test pharmaceutical formulation was considered acceptable if no significant change in various analytical properties was detected from the initial time point for the indicated storage period at the different temperatures. Physical stability of a test pharmaceutical formulation was considered acceptable if upon visual assessment no particles were observed and upon assessment by Thioflavin T fluorescence microscopy no fibril or gel formation was observed.

$PEG_{20\ kDa}$-B28-insulin lispro formulations containing 0.5 mole zinc per mole of $PEG_{20\ kDa}$-B28-insulin lispro, 16 mg/mL glycerin, 3.15 mg/mL m-cresol, buffered with either phosphate or citrate at pH 7.0 or pH 6.5, respectively, were prepared and tested for both chemical and physical stability. Similar formulations without zinc were tested to evaluate the impact of zinc on stability. Samples at 35° C. formed gel particles after approximately 1 month of storage and samples at 25° C. showed significant number of particles/bubbles formation after approximately two months of storage. Both citrate and phosphate buffered as well as zinc/no zinc formulations showed similar chemical/physical stability at the accelerated 35° C. condition although citrate buffer samples appeared to be worse than phosphate buffered samples when assessed visually. Insulin lispro control formulation remained clear. Both citrate and phosphate buffered formulations demonstrated an acceptable chemical stability at 5° C. for at least 13 months.

Subsequent investigations indicated that the phenolic preservative, m-cresol, promoted gellation when combined with $PEG_{20\ kDa}$-B28-insulin lispro composed and exposed to high temperature (>25° C.). Interestingly, when m-cresol was added to mPEG alone (activated or non-activated) gel particles did not result upon exposure to high temperature.

When the prototypical formulations of insulin lispro did not confer acceptable stability to $PEG_{20\ kDa}$-B28-insulin lispro compounds at elevated temperatures, pharmaceutical compositions comprising $PEG_{20\ kDa}$-$B28_{(\sim 95\%)}/A1_{(\sim 5\%)}$-insulin lispro compounds demonstrating improved chemical and physical stability and suitable for commercialization as a parenterally administered pharmaceutical formulation were developed.

The following formulations of $PEG_{20\ kDa}$-$B28_{(\sim 95\%)}/A1_{(\sim 5\%)}$-insulin lispro (15 mg/mL) demonstrated acceptable chemical and physical stability for one week at 40° C., for one month at 30° C., for three months at 25° C., and for over eight months at 5° C.:

1) 16 mM TRIS buffer, pH 7.0-8.0, 10 mM calcium chloride, 20 mg/mL sugar (sucrose or trehalose), 3 mg/mL (28 mM) m-cresol, and 0.5 mole zinc per 1.0 mole $PEG_{20\ kDa}$-$B^{28}_{(\sim 95\%)}/A1_{(\sim 5\%)}$-insulin lispro 2) 16 mM TRIS buffer, pH 7.0-8.0, 10 mM calcium chloride, 3 mg/mL poloxamer, 3 mg/mL (28 mM) m-cresol, and 0.5 mole zinc per 1.0 mole $PEG_{20\ kDa}$-$B28_{(\sim 95\%)}/A1_{(\sim 5\%)}$-insulin lispro 3) 5 mM phosphate buffer, pH 7.0, 130 mM glycerine, 3 mg/mL (28 mM) m-cresol, 3 mg/mL poloxamer, 0.3 mole zinc per 1.0 mole of $PEG_{20\ kDa}$-$B^{28}_{(\sim 95\%)}/A1_{(\sim 5\%)}$-insulin lispro Formulations of $PEG_{20\ kDa}$-$B28_{(\sim 95\%)}/A1_{(\sim 5\%)}$-insulin lispro containing hexamer promoting excipients, e.g., zinc, m-cresol, and calcium generally exhibited greater physical and chemical stability, especially at elevated temperatures. Addition of calcium, chloride and/or NaCl to $PEG_{20\ kDa}$-$B28_{(\sim 95\%)}/A1_{(\sim 5\%)}$-insulin lispro formulations containing zinc and m-cresol further enhanced the physical stability of formulations exposed to temperatures of 40° C. or greater. Furthermore, phosphate and citrate buffered formulations generally exhibited less physical stability than TRIS buffered formulations.

---

We claim:

1. A PEGylated insulin lispro compound of the formula: P-[(A)-(B)], or a pharmaceutically acceptable salt thereof, wherein;
   A is the A-chain of insulin lispro (SEQ ID NO: 1);
   B is the B-chain of insulin lispro (SEQ ID NO: 3); and
   P is a PEG having a molecular weight in the range from about 17.5 kDa to about 25 kDa, and wherein A and B contain a disulfide bond between the cysteine at position 7 of A (SEQ ID NO: 1) and the cysteine at position 7 of B (SEQ ID NO: 3), a disulfide bond between the cysteine at position 20 of A (SEQ ID NO: 1) and the cysteine at position 19 of B (SEQ ID NO: 3), and a disulfide bond between the cysteine at position 6 of A (SEQ ID NO: 1) and the cysteine at position 11 of A (SEQ ID NO: 1) and P is attached via a urethane covalent bond to the epsilon-amino group of the lysine at position 28 of B.

2. A pharmaceutical composition comprising a PEGylated insulin lispro compound of the formula: P-[(A)-(B)], or a pharmaceutically acceptable salt thereof, wherein:
   A is the A-chain of insulin lispro (SEQ ID NO: 1);
   B is the B-chain of insulin lispro (SEQ ID NO: 3); and
   P is a PEG having a molecular weight in the range from about 17.5 kDa to about 25 kDa, and wherein A and B contain a disulfide bond between the cysteine at position 7 of A (SEQ ID NO: 1) and the cysteine at position 7 of B (SEQ ID NO: 3), a disulfide bond between the cysteine at position 20 of A (SEQ ID NO: 1) and the cysteine at position 19 of B (SEQ ID NO: 3), and a disulfide bond between the cysteine at position 6 of A (SEQ ID NO: 1) and the cysteine at position 11 of A (SEQ ID NO: 1) and P is attached via a urethane covalent bond to the epsilon-amino group of the lysine at position 28 of B, and one or more pharmaceutically acceptable excipients, diluents, or carriers.

3. The PEGylated insulin lispro compound of claim 1 wherein the PEG has a molecular weight of about 20 kDa.

4. The pharmaceutical composition according to claim 2 wherein the PEG has a molecular weight of about 20 kDa.

* * * * *

UNITED STATES PATENT AND TRADEMARK OFFICE
CERTIFICATE OF CORRECTION

| | | |
|---|---|---|
| PATENT NO. | : 9,050,371 B2 | Page 1 of 1 |
| APPLICATION NO. | : 12/481111 | |
| DATED | : June 9, 2015 | |
| INVENTOR(S) | : Beals et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 672 days.

Signed and Sealed this
Fifth Day of January, 2016

Michelle K. Lee
*Director of the United States Patent and Trademark Office*